US012685317B2

(12) United States Patent
Cramer et al.

(10) Patent No.: US 12,685,317 B2
(45) Date of Patent: Jul. 21, 2026

(54) COMBINATION OF NONMALTOGENIC EXOAMYLASE AND GLUCOAMYLASE FOR IMPROVING BREAD RESILIENCE AND REDUCING AMOUNT OF ADDED SUGARS

(71) Applicants: INTERNATIONAL N&H DENMARK APS, Kongens Lyngby (DK); DANISCO US INC., Palo Alto, CA (US)

(72) Inventors: Jacob Flyvholm Cramer, Højbjerg (DK); Morgan Louise Gifford, Merriam, KS (US); Svend Haaning, Galten (DK); Lene Kragh, Højbjerg (DK); Vinni Høyer Lillelund, Bjerringbro (DK); Donald E. Ward, Overland Park, KS (US)

(73) Assignee: INTERNATIONAL N&H DENMARK APS, Kongens Lyngby (DK)

( * ) Notice: Subject to any disclaimer, the term of this patent is extended or adjusted under 35 U.S.C. 154(b) by 625 days.

(21) Appl. No.: 18/026,395

(22) PCT Filed: Sep. 21, 2021

(86) PCT No.: PCT/US2021/051241

§ 371 (c)(1),
(2) Date: Mar. 15, 2023

(87) PCT Pub. No.: WO2022/061276

PCT Pub. Date: Mar. 24, 2022

(65) Prior Publication Data

US 2023/0404088 A1      Dec. 21, 2023

Related U.S. Application Data

(60) Provisional application No. 63/080,984, filed on Sep. 21, 2020.

(51) Int. Cl.
| *A21D 8/04* | (2006.01) |
| *C12N 9/26* | (2006.01) |
| *C12N 9/34* | (2006.01) |

(52) U.S. Cl.
CPC ........... *A21D 8/042* (2013.01); *C12N 9/2414* (2013.01); *C12N 9/2428* (2013.01); *C12Y 302/01001* (2013.01); *C12Y 302/01003* (2013.01)

(58) Field of Classification Search
CPC .... A21D 8/042; C12N 9/2414; C12N 9/2428; C12Y 302/01001; C12Y 302/01003
See application file for complete search history.

(56) References Cited

U.S. PATENT DOCUMENTS

| 5,281,526 | A | 1/1994 | Good et al. |
| 6,022,725 | A | 2/2000 | Fowler et al. |
| 2009/0202675 | A1 | 8/2009 | Derkx et al. |
| 2009/0214706 | A1* | 8/2009 | Berg ....................... A23L 29/35 |
| | | | 426/54 |
| 2011/0136197 | A1 | 6/2011 | Dodge et al. |
| 2012/0164695 | A1* | 6/2012 | Aehle .................. C12N 9/2428 |
| | | | 435/252.31 |
| 2012/0190075 | A1* | 7/2012 | Kragh .................. C12N 9/2417 |
| | | | 435/99 |
| 2018/0242598 | A1 | 8/2018 | Feng et al. |

FOREIGN PATENT DOCUMENTS

| EP | 0238023 B1 | 12/1993 |
| WO | 199117243 A1 | 11/1991 |
| WO | 199950399 A2 | 10/1999 |
| WO | 2005001036 A2 | 1/2005 |
| WO | 2011127802 A1 | 10/2011 |
| WO | 2016138315 A1 | 9/2016 |
| WO | 2018151185 A1 | 8/2018 |
| WO | 2018164737 A1 | 9/2018 |

OTHER PUBLICATIONS

Campbell et al, "Improved transformation efficiency of Aspergillus niger using the homologous niaD gene for nitrate reductase", Curr Genet, vol. 16, 1989, pp. 53-56.
Cao et al, "Penicillopepsin-JT2, a recombinant enzyme from Penicillium janthinellum and the contribution of a hydrogen bond in subsite S3 to kcat", Protein Science, vol. 9, 2000, pp. 991-1001.
Database GenBank [Online] 2002, Nielsen BR et al: "glucoamylase [Rasamsonia emersonii]", XP55872425, Database accession No. CAC28076.1.
FGSC, Catalogue of Strains, University of Missouri, at www.fgsc. net (last modified Jan. 17, 2007).
Gornall et al, "Determination of serum proteins by means of the biuret reaction", J Biol Chem., Feb. 1949, vol. 177, No. 2, pp. 751-766.
Harrison et al, "Employing Site-Specific Recombination for Conditional Genetic Analysis in Sinorhizobium meliloti", Applied and Environmental Microbiology, vol. 77, No. 12, Jun. 2011, pp. 3916-3922.
International Search Report from PCT App. No. PCT/US2021/ 051241 dated Dec. 23, 2021, 5 pages.
Liu et al, "Improved heterologous gene expression in Trichoderma reesei by cellobiohydrolase I gene (cbh1) promoter optimization", Acta Biochim. Biophys. Sin (Shanghai), vol. 40, No. 2, 2008, pp. 158-165.
Te'o et al, "Biolistic transformation of Trichoderma reesei using the Bio-Rad seven barrels Hepta Adaptor system", Journal of Microbiological Methods, vol. 51, 2002, pp. 393-399.
Thompson et al., "Clustal W: improving the sensitivity of progressive multiple sequence alignment through sequence weighting, position-specific gap penalties and weight matrix choice", Nucleic Acids Research, 1994, vol. 22, No. 22, pp. 4673-4680.

(Continued)

*Primary Examiner* — Jenna A Watts

(57) ABSTRACT

This invention relates to polypeptides, more specifically non-maltogenic alpha-amylase and glucoamylase polypeptides, and their uses in providing baked products with enhanced resilience.

6 Claims, No Drawings

Specification includes a Sequence Listing.

(56)          References Cited

OTHER PUBLICATIONS

Weichselbaum, "An Accurate and Rapid Method for the Determi-
nation of Proteins in Small Amounts of Blood Serum and Plasma",
American Journal of Clinical Pathology, Mar. 1946, vol. 16, Issue
3, pp. 40-49.

* cited by examiner

SEQUENCE LISTING

<160> NUMBER OF SEQ ID NOS: 6

<210> SEQ ID NO 1
<211> LENGTH: 430
<212> TYPE: PRT
<213> ORGANISM: Pseudomonas saccarophilia

<400> SEQUENCE: 1

```
Ala Asp Gln Ala Gly Lys Ser Pro Ala Gly Val Arg Tyr His Gly Gly
1               5                   10                  15

Asp Glu Ile Ile Leu Gln Gly Phe His Trp Asn Val Val Arg Glu Ala
            20                  25                  30

Pro Tyr Asn Trp Tyr Asn Ile Leu Arg Gln Gln Ala Ser Thr Ile Ala
        35                  40                  45

Ala Asp Gly Phe Ser Ala Ile Trp Met Pro Val Pro Trp Arg Asp Phe
    50                  55                  60

Ser Ser Trp Thr Asp Gly Asp Lys Ser Gly Gly Gly Glu Gly Tyr Phe
65                  70                  75                  80

Trp His Asp Phe Asn Lys Asn Gly Arg Tyr Gly Ser Asp Ala Gln Leu
                85                  90                  95

Arg Gln Ala Ala Gly Ala Leu Gly Gly Ala Gly Val Lys Val Leu Tyr
            100                 105                 110

Asp Val Val Pro Asn His Met Asn Arg Phe Tyr Pro Asp Lys Glu Ile
            115                 120                 125

Asn Leu Pro Ala Gly Gln Arg Phe Trp Arg Asn Asp Cys Pro Asp Pro
        130                 135                 140

Gly Asn Gly Pro Asn Asp Cys Asp Asp Gly Asp Arg Phe Leu Gly Gly
145                 150                 155                 160

Glu Ala Asp Leu Asn Thr Gly His Pro Gln Ile Tyr Gly Met Phe Arg
                165                 170                 175

Asp Glu Phe Thr Asn Leu Arg Ser Gly Tyr Gly Ala Gly Gly Phe Arg
            180                 185                 190

Phe Asp Phe Val Arg Gly Tyr Ala Pro Glu Arg Val Asp Ser Trp Met
            195                 200                 205

Ser Asp Ser Ala Asp Ser Ser Phe Cys Val Gly Glu Leu Trp Lys Glu
        210                 215                 220

Pro Ser Glu Tyr Pro Pro Trp Asp Trp Arg Asn Thr Ala Ser Trp Gln
225                 230                 235                 240

Gln Ile Ile Lys Asp Trp Ser Asp Arg Ala Lys Cys Pro Val Phe Asp
            245                 250                 255

Phe Ala Leu Lys Glu Arg Met Gln Asn Gly Ser Val Ala Asp Trp Lys
            260                 265                 270

His Gly Leu Asn Gly Asn Pro Asp Pro Arg Trp Arg Glu Val Ala Val
        275                 280                 285

Thr Phe Val Asp Asn His Asp Thr Gly Tyr Ser Pro Gly Gln Asn Gly
    290                 295                 300

Gly Gln His Lys Trp Pro Leu Gln Asp Gly Leu Ile Arg Gln Ala Tyr
305                 310                 315                 320

Ala Tyr Ile Leu Thr Ser Pro Gly Thr Pro Val Val Tyr Trp Pro His
                325                 330                 335

Met Tyr Asp Trp Gly Tyr Gly Asp Phe Ile Arg Gln Leu Ile Gln Val
            340                 345                 350

Arg Arg Thr Ala Gly Val Arg Ala Asp Ser Ala Ile Ser Phe His Ser
        355                 360                 365
```

```
Gly Tyr Ser Gly Leu Val Ala Thr Val Ser Gly Ser Gln Gln Thr Leu
    370                 375                 380

Val Val Ala Leu Asn Ser Asp Leu Ala Asn Pro Gly Gln Val Ala Ser
385                 390                 395                 400

Gly Ser Phe Ser Glu Ala Val Asn Ala Ser Asn Gly Gln Val Arg Val
                405                 410                 415

Trp Arg Ser Gly Ser Gly Asp Gly Gly Gly Asn Asp Gly Gly
                420                 425                 430

<210> SEQ ID NO 2
<211> LENGTH: 430
<212> TYPE: PRT
<213> ORGANISM: Pseudomonas saccharophilia

<400> SEQUENCE: 2

Met Asp Gln Ala Gly Lys Ser Pro Ala Gly Val Arg Tyr His Gly Gly
1                   5                   10                  15

Asp Glu Ile Ile Leu Gln Gly Phe His Trp Asn Val Val Arg Glu Ala
                20                  25                  30

Pro Tyr Asn Trp Tyr Asn Ile Leu Arg Gln Lys Ala Ser Thr Ile Ala
            35                  40                  45

Ala Asp Gly Phe Ser Ala Ile Trp Met Pro Val Pro Trp Arg Asp Phe
        50                  55                  60

Ser Ser Trp Thr Asp Gly Asp Lys Ser Gly Gly Gly Glu Gly Tyr Phe
65                  70                  75                  80

Trp His Asp Phe Asn Lys Asn Gly Leu Tyr Gly Ser Asp Ala Gln Leu
                85                  90                  95

Arg Gln Ala Ala Gly Ala Leu Gly Gly Ala Gly Val Lys Val Leu Tyr
                100                 105                 110

Asp Val Val Pro Asn His Met Asn Arg Phe Tyr Pro Asp Lys Glu Ile
            115                 120                 125

Asn Leu Pro Ala Gly Gln Arg Phe Trp Arg Asn Asp Cys Pro Asp Pro
        130                 135                 140

Gly Asn Gly Pro Asn Asp Cys Asp Asp Gly Asp Arg Phe Leu Gly Gly
145                 150                 155                 160

Glu Ala Asp Leu Asn Thr Gly His Pro Gln Ile Tyr Gly Met Phe Arg
                165                 170                 175

Asp Glu Phe Thr Asn Leu Arg Ser Gly Tyr Gly Ala Gly Gly Phe Arg
            180                 185                 190

Phe Asp Phe Val Arg Gly Tyr Ala Pro Glu Arg Val Asp Leu Trp Met
        195                 200                 205

Ser Asp Ser Ala Asp Ser Ser Phe Cys Val Gly Glu Leu Trp Lys Lys
    210                 215                 220

Pro Ser Glu Tyr Pro Pro Trp Asp Trp Arg Asn Arg Ala Ser Trp Gln
225                 230                 235                 240

Glu Ile Ile Lys Asp Trp Ser Asp Arg Ala Lys Cys Pro Val Phe Asp
                245                 250                 255

Phe Ala Leu Lys Glu Arg Met Gln Asn Gly Ser Val Ala Asp Trp Lys
            260                 265                 270

His Gly Leu Asn Gly Asn Pro Asp Pro Arg Trp Arg Glu Val Ala Val
        275                 280                 285

Thr Phe Val Asp Asn His Asp Thr Gly Tyr Ser Pro Gly Gln Asn Gly
    290                 295                 300

Gly Gln His Lys Trp Pro Leu Pro Asp Gly Leu Ile Arg Gln Ala Tyr
305                 310                 315                 320
```

-continued

```
Ala Tyr Ile Leu Thr Ser Pro Gly Thr Pro Val Val Tyr Trp Pro His
            325             330             335

Met Tyr Asp Trp Gly Tyr Gly Asp Phe Ile Arg Gln Leu Ile Gln Val
            340             345             350

Arg Arg Thr Ala Gly Val Arg Ala Asp Ser Ala Ile Ser Phe His Ser
            355             360             365

Gly Tyr Ser Gly Leu Val Ala Thr Val Ser Gly Ser Gln Gln Thr Leu
            370             375             380

Val Val Ala Leu Asn Ser Asp Leu Asp Asn Pro Gly Gln Val Ala Ser
385             390             395             400

Gly Ser Phe Ser Glu Ala Val Asn Ala Glu Asn Gly Gln Val Arg Val
            405             410             415

Trp Arg Ser Gly Ser Gly Asp Gly Gly Gly Asn Asp Gly Gly
            420             425             430

<210> SEQ ID NO 3
<211> LENGTH: 592
<212> TYPE: PRT
<213> ORGANISM: Penicillium sp.

<400> SEQUENCE: 3

Ser Pro Thr Ser Lys Asp Gly Asn Leu Ala Ser Tyr Ile Ala Lys Glu
1               5               10              15

Gly Gln Arg Ser Ile Val Gly Ile Thr Glu Asn Leu Gly Gly Lys Gly
            20              25              30

Ser Lys Thr Pro Gly Thr Ala Ala Gly Leu Phe Ile Ala Ser Pro Asn
            35              40              45

Met Ala Asn Pro Asn Tyr Tyr Tyr Thr Trp Thr Arg Asp Ser Ala Leu
            50              55              60

Thr Phe Lys Cys Leu Ile Asp Leu Phe Glu Thr Ser Asp Gln Asp Tyr
65              70              75              80

Ile Ser Arg Lys Glu Leu Glu Thr Asp Ile Arg Asn Tyr Val Ser Ser
            85              90              95

Gln Ala Val Leu Gln Asn Val Ser Asn Pro Ser Gly Thr Leu Lys Asp
            100             105             110

Gly Ser Gly Leu Gly Glu Pro Lys Phe Glu Ile Asp Leu Asn Pro Phe
            115             120             125

Ser Gly Ser Trp Gly Arg Pro Gln Arg Asp Gly Pro Ala Leu Arg Ala
            130             135             140

Thr Ala Met Ile Thr Tyr Ala Asp Trp Leu Val Ser His Gly Gln Lys
145             150             155             160

Ser Glu Ala Thr Asn Ile Met Trp Pro Ile Ile Ala Asn Asp Leu Ala
            165             170             175

Tyr Val Gly Gln Tyr Trp Asn Lys Thr Gly Phe Asp Leu Trp Glu Glu
            180             185             190

Val Asp Gly Ser Ser Phe Tyr Thr Leu Ala Val Gln His Arg Ala Leu
            195             200             205

Val Gln Gly Ala Ser Leu Ala Lys Lys Leu Gly Lys Ser Cys Thr Ala
            210             215             220

Cys Val Ser Gln Ala Pro Gln Ile Leu Cys Phe Leu Gln Ser Phe Trp
225             230             235             240

Asn Gly Asn Tyr Ile Thr Ala Asn Ile Asn Leu Asp Thr Ser Arg Ser
            245             250             255

Gly Ile Asp Leu Asn Ser Ile Leu Gly Ser Ile His Thr Phe Asp Pro
```

-continued

```
                 260                 265                 270
Glu Ala Ser Cys Asp Asp Ser Thr Phe Gln Pro Cys Ser Ala Arg Ala
            275                 280                 285
Leu Ala Asn His Lys Val Tyr Val Asp Ala Phe Arg Ser Ile Tyr Gly
            290                 295                 300
Val Asn Ala Gly Leu Ser Asn Gly Thr Ala Ala Asn Val Gly Arg Tyr
305                 310                 315                 320
Pro Glu Asp Val Tyr Gln Gly Gly Asn Pro Trp Tyr Leu Ala Thr Leu
                325                 330                 335
Ala Ala Ala Glu Leu Leu Tyr Asp Ala Leu Tyr Gln Trp Asn Gln Ile
            340                 345                 350
Gly Lys Leu Asp Val Thr Lys Thr Ser Leu Ala Phe Phe Lys Asp Phe
            355                 360                 365
Asp Ala Ala Val Lys Thr Gly Thr Tyr Ser Ala His Ser Ser Ala Tyr
            370                 375                 380
Arg Thr Leu Thr Ser Ala Ile Arg Thr Tyr Ala Asp Asp Phe Ile Ser
385                 390                 395                 400
Leu Val Gln His Tyr Thr Pro Ser Asn Gly Ser Leu Ala Glu Gln Tyr
                405                 410                 415
Asp Arg Asp Thr Gly Ile Pro Leu Ser Ala Asn Asp Leu Thr Trp Ser
            420                 425                 430
Tyr Ala Ser Phe Ile Thr Ala Ile Glu Arg Arg Ala Ser Val Val Pro
            435                 440                 445
Ala Ser Trp Gly Glu Lys Ser Ala Asn Val Val Pro Thr Thr Cys Ser
    450                 455                 460
Ala Ser Pro Val Thr Gly Thr Tyr Val Ala Ala Thr Ser Val Phe Pro
465                 470                 475                 480
Thr Thr Thr Gly Cys Val Pro Ala Thr Ser Ile Val Pro Ile Thr Phe
                485                 490                 495
Tyr Leu Thr Glu Ser Thr Phe Tyr Gly Glu Asn Val Tyr Met Thr Gly
                500                 505                 510
Asn Ile Ser Ala Leu Gly Asn Trp Asp Thr Ser Ser Gly Phe Pro Leu
            515                 520                 525
Thr Ala Asn Leu Tyr Thr Asp Ser Asp His Leu Trp Phe Ala Ser Val
            530                 535                 540
Glu Leu Val Pro Ala Gly Thr Pro Phe Glu Tyr Lys Tyr Tyr Lys Val
545                 550                 555                 560
Glu Pro Asn Gly Thr Val Ile Trp Glu Asn Gly Glu Asn Arg Val Tyr
                565                 570                 575
Val Ala Pro Thr Gly Cys Pro Ile Gln Pro Ser Gln Thr Asp Ile Trp
                580                 585                 590
```

<210> SEQ ID NO 4
<211> LENGTH: 591
<212> TYPE: PRT
<213> ORGANISM: Rasamsonia emersonii

<400> SEQUENCE: 4

```
Ala Thr Gly Ser Leu Asp Ser Phe Leu Ala Thr Glu Thr Pro Ile Ala
1               5                   10                  15
Leu Gln Gly Val Leu Asn Asn Ile Gly Pro Asn Gly Ala Asp Val Ala
                20                  25                  30
Gly Ala Ser Ala Gly Ile Val Val Ala Ser Pro Ser Arg Ser Asp Pro
            35                  40                  45
```

```
Asn Tyr Phe Tyr Ser Trp Thr Arg Asp Ala Ala Leu Thr Ala Lys Tyr
    50              55              60

Leu Val Asp Ala Phe Ile Ala Gly Asn Lys Asp Leu Glu Gln Thr Ile
65              70              75              80

Gln Gln Tyr Ile Ser Ala Gln Ala Lys Val Gln Thr Ile Ser Asn Pro
            85              90              95

Ser Gly Asp Leu Ser Thr Gly Gly Leu Gly Glu Pro Lys Phe Asn Val
            100             105             110

Asn Glu Thr Ala Phe Thr Gly Pro Trp Gly Arg Pro Gln Arg Asp Gly
            115             120             125

Pro Ala Leu Arg Ala Thr Ala Leu Ile Ala Tyr Ala Asn Tyr Leu Ile
    130             135             140

Asp Asn Gly Glu Ala Ser Thr Ala Asp Glu Ile Ile Trp Pro Ile Val
145             150             155             160

Gln Asn Asp Leu Ser Tyr Val Thr Gln Tyr Trp Asn Ser Ser Thr Phe
            165             170             175

Asp Leu Trp Glu Glu Val Glu Gly Ser Ser Phe Phe Thr Thr Ala Val
            180             185             190

Gln His Arg Ala Leu Val Glu Gly Asn Ala Leu Ala Thr Arg Leu Asn
    195             200             205

His Thr Cys Ser Asn Cys Val Ser Gln Ala Pro Gln Val Leu Cys Phe
    210             215             220

Leu Gln Ser Tyr Trp Thr Gly Ser Tyr Val Leu Ala Asn Phe Gly Gly
225             230             235             240

Ser Gly Arg Ser Gly Lys Asp Val Asn Ser Ile Leu Gly Ser Ile His
            245             250             255

Thr Phe Asp Pro Ala Gly Gly Cys Asp Asp Ser Thr Phe Gln Pro Cys
            260             265             270

Ser Ala Arg Ala Leu Ala Asn His Lys Val Val Thr Asp Ser Phe Arg
    275             280             285

Ser Ile Tyr Ala Ile Asn Ser Gly Ile Ala Glu Gly Ser Ala Val Ala
    290             295             300

Val Gly Arg Tyr Pro Glu Asp Val Tyr Gln Gly Gly Asn Pro Trp Tyr
305             310             315             320

Leu Ala Thr Ala Ala Ala Ala Glu Gln Leu Tyr Asp Ala Ile Tyr Gln
            325             330             335

Trp Lys Lys Ile Gly Ser Ile Ser Ile Thr Asp Val Ser Leu Pro Phe
            340             345             350

Phe Gln Asp Ile Tyr Pro Ser Ala Ala Val Gly Thr Tyr Asn Ser Gly
            355             360             365

Ser Thr Thr Phe Asn Asp Ile Ile Ser Ala Val Gln Thr Tyr Gly Asp
    370             375             380

Gly Tyr Leu Ser Ile Val Glu Lys Tyr Thr Pro Ser Asp Gly Ser Leu
385             390             395             400

Thr Glu Gln Phe Ser Arg Thr Asp Gly Thr Pro Leu Ser Ala Ser Ala
            405             410             415

Leu Thr Trp Ser Tyr Ala Ser Leu Leu Thr Ala Ser Ala Arg Arg Gln
            420             425             430

Ser Val Val Pro Ala Ser Trp Gly Glu Ser Ser Ala Ser Ser Val Pro
    435             440             445

Ala Val Cys Ser Ala Thr Ser Ala Thr Gly Pro Tyr Ser Thr Ala Thr
    450             455             460

Asn Thr Val Trp Pro Ser Ser Gly Ser Gly Ser Ser Thr Thr Thr Ser
```

-continued

```
465                    470                    475                    480

Ser Ala Pro Cys Thr Thr Pro Thr Ser Val Ala Val Thr Phe Asp Glu
                485                    490                    495

Ile Val Ser Thr Ser Tyr Gly Glu Thr Ile Tyr Leu Ala Gly Ser Ile
            500                    505                    510

Pro Glu Leu Gly Asn Trp Ser Thr Ala Ser Ala Ile Pro Leu Arg Ala
            515                    520                    525

Asp Ala Tyr Thr Asn Ser Asn Pro Leu Trp Tyr Val Thr Val Asn Leu
            530                    535                    540

Pro Pro Gly Thr Ser Phe Glu Tyr Lys Phe Phe Lys Asn Gln Thr Asp
545                    550                    555                    560

Gly Thr Ile Val Trp Glu Asp Asp Pro Asn Arg Ser Tyr Thr Val Pro
                565                    570                    575

Ala Tyr Cys Gly Gln Thr Thr Ala Ile Leu Asp Asp Ser Trp Gln
                580                    585                    590

<210> SEQ ID NO 5
<211> LENGTH: 540
<212> TYPE: PRT
<213> ORGANISM: Trichoderma reesei

<400> SEQUENCE: 5

Met His Val Leu Ser Thr Ala Val Leu Leu Gly Ser Val Ala Val Gln
1               5                   10                  15

Lys Val Leu Gly Arg Pro Gly Ser Ser Gly Leu Ser Asp Val Thr Lys
                20                  25                  30

Arg Ser Val Asp Asp Phe Ile Ser Thr Glu Thr Pro Ile Ala Leu Asn
            35                  40                  45

Asn Leu Leu Cys Asn Val Gly Pro Asp Gly Cys Arg Ala Phe Gly Thr
        50                  55                  60

Ser Ala Gly Ala Val Ile Ala Ser Pro Ser Thr Ile Asp Pro Asp Tyr
65                  70                  75                  80

Tyr Tyr Met Trp Thr Arg Asp Ser Ala Leu Val Phe Lys Asn Leu Ile
                85                  90                  95

Asp Arg Phe Thr Glu Thr Tyr Asp Ala Gly Leu Gln Arg Arg Ile Glu
            100                 105                 110

Gln Tyr Ile Thr Ala Gln Val Thr Leu Gln Gly Leu Ser Asn Pro Ser
            115                 120                 125

Gly Ser Leu Ala Asp Gly Ser Gly Leu Gly Glu Pro Lys Phe Glu Leu
        130                 135                 140

Thr Leu Lys Pro Phe Thr Gly Asn Trp Gly Arg Pro Gln Arg Asp Gly
145                 150                 155                 160

Pro Ala Leu Arg Ala Ile Ala Leu Ile Gly Tyr Ser Lys Trp Leu Ile
                165                 170                 175

Asn Asn Asn Tyr Gln Ser Thr Val Ser Asn Val Ile Trp Pro Ile Val
                180                 185                 190

Arg Asn Asp Leu Asn Tyr Val Ala Gln Tyr Trp Asn Gln Thr Gly Phe
            195                 200                 205

Asp Leu Trp Glu Glu Val Asn Gly Ser Ser Phe Phe Thr Val Ala Asn
        210                 215                 220

Gln His Arg Ala Leu Val Glu Gly Ala Thr Leu Ala Ala Thr Leu Gly
225                 230                 235                 240

Gln Ser Gly Ser Ala Tyr Ser Ser Val Ala Pro Gln Val Leu Cys Phe
                245                 250                 255
```

```
Leu Gln Arg Phe Trp Val Ser Ser Gly Gly Tyr Val Asp Ser Asn Ile
            260                 265                 270

Asn Thr Asn Glu Gly Arg Thr Gly Lys Asp Val Asn Ser Val Leu Thr
            275                 280                 285

Ser Ile His Thr Phe Asp Pro Asn Leu Gly Cys Asp Ala Gly Thr Phe
            290                 295                 300

Gln Pro Cys Ser Asp Lys Ala Leu Ser Asn Leu Lys Val Val Val Asp
305                 310                 315                 320

Ser Phe Arg Ser Ile Tyr Gly Val Asn Lys Gly Ile Pro Ala Gly Ala
                325                 330                 335

Ala Val Ala Ile Gly Arg Tyr Ala Glu Asp Val Tyr Tyr Asn Gly Asn
                340                 345                 350

Pro Trp Tyr Leu Ala Thr Phe Ala Ala Ala Glu Gln Leu Tyr Asp Ala
                355                 360                 365

Ile Tyr Val Trp Lys Lys Thr Gly Ser Ile Thr Val Thr Ala Thr Ser
            370                 375                 380

Leu Ala Phe Phe Gln Glu Leu Val Pro Gly Val Thr Ala Gly Thr Tyr
385                 390                 395                 400

Ser Ser Ser Ser Ser Thr Phe Thr Asn Ile Ile Asn Ala Val Ser Thr
                405                 410                 415

Tyr Ala Asp Gly Phe Leu Ser Glu Ala Ala Lys Tyr Val Pro Ala Asp
                420                 425                 430

Gly Ser Leu Ala Glu Gln Phe Asp Arg Asn Ser Gly Thr Pro Leu Ser
                435                 440                 445

Ala Leu His Leu Thr Trp Ser Tyr Ala Ser Phe Leu Thr Ala Thr Ala
            450                 455                 460

Arg Arg Ala Gly Ile Val Pro Pro Ser Trp Ala Asn Ser Ser Ala Ser
465                 470                 475                 480

Thr Ile Pro Ser Thr Cys Ser Gly Ala Ser Val Val Gly Ser Tyr Ser
                485                 490                 495

Arg Pro Thr Ala Thr Ser Phe Pro Pro Ser Gln Thr Pro Lys Pro Gly
                500                 505                 510

Val Pro Ser Gly Thr Pro Tyr Thr Pro Leu Pro Cys Ala Thr Pro Thr
                515                 520                 525

Ser Val Ala Val Thr Phe His Glu Leu Val Ser Thr
            530                 535                 540
```

```
<210> SEQ ID NO 6
<211> LENGTH: 686
<212> TYPE: PRT
<213> ORGANISM: Bacillus stearothermophilus

<400> SEQUENCE: 6
```

```
Ser Ser Ser Ala Ser Val Lys Gly Asp Val Ile Tyr Gln Ile Ile Ile
1                 5                 10                  15

Asp Arg Phe Tyr Asp Gly Asp Thr Thr Asn Asn Asn Pro Ala Lys Ser
            20                  25                  30

Tyr Gly Leu Tyr Asp Pro Thr Lys Ser Lys Trp Lys Met Tyr Trp Gly
            35                  40                  45

Gly Asp Leu Glu Gly Val Arg Gln Lys Leu Pro Tyr Leu Lys Gln Leu
            50                  55                  60

Gly Val Thr Thr Ile Trp Leu Ser Pro Val Leu Asp Asn Leu Asp Thr
65                  70                  75                  80

Leu Ala Gly Thr Asp Asn Thr Gly Tyr His Gly Tyr Trp Thr Arg Asp
                85                  90                  95
```

-continued

```
Phe Lys Gln Ile Glu Glu His Phe Gly Asn Trp Thr Thr Phe Asp Thr
            100                 105                 110

Leu Val Asn Asp Ala His Gln Asn Gly Ile Lys Val Ile Val Asp Phe
            115                 120                 125

Val Pro Asn His Ser Thr Pro Phe Lys Ala Asn Asp Ser Thr Phe Ala
            130                 135                 140

Glu Gly Gly Ala Leu Tyr Asn Asn Gly Thr Tyr Met Gly Asn Tyr Phe
145                 150                 155                 160

Asp Asp Ala Thr Lys Gly Tyr Phe His His Asn Gly Asp Ile Ser Asn
                165                 170                 175

Trp Asp Asp Arg Tyr Glu Ala Gln Trp Lys Asn Phe Thr Asp Pro Ala
                180                 185                 190

Gly Phe Ser Leu Ala Asp Leu Ser Gln Glu Asn Gly Thr Ile Ala Gln
                195                 200                 205

Tyr Leu Thr Asp Ala Ala Val Gln Leu Val Ala His Gly Ala Asp Gly
            210                 215                 220

Leu Arg Ile Asp Ala Val Lys His Phe Asn Ser Gly Phe Ser Lys Ser
225                 230                 235                 240

Leu Ala Asp Lys Leu Tyr Gln Lys Lys Asp Ile Phe Leu Val Gly Glu
                245                 250                 255

Trp Tyr Gly Asp Asp Pro Gly Thr Ala Asn His Leu Glu Lys Val Arg
                260                 265                 270

Tyr Ala Asn Asn Ser Gly Val Asn Val Leu Asp Phe Asp Leu Asn Thr
            275                 280                 285

Val Ile Arg Asn Val Phe Gly Thr Phe Thr Gln Thr Met Tyr Asp Leu
            290                 295                 300

Asn Asn Met Val Asn Gln Thr Gly Asn Glu Tyr Lys Tyr Lys Glu Asn
305                 310                 315                 320

Leu Ile Thr Phe Ile Asp Asn His Asp Met Ser Arg Phe Leu Ser Val
                325                 330                 335

Asn Ser Asn Lys Ala Asn Leu His Gln Ala Leu Ala Phe Ile Leu Thr
            340                 345                 350

Ser Arg Gly Thr Pro Ser Ile Tyr Tyr Gly Thr Glu Gln Tyr Met Ala
            355                 360                 365

Gly Gly Asn Asp Pro Tyr Asn Arg Gly Met Met Pro Ala Phe Asp Thr
            370                 375                 380

Thr Thr Thr Ala Phe Lys Glu Val Ser Thr Leu Ala Gly Leu Arg Arg
385                 390                 395                 400

Asn Asn Ala Ala Ile Gln Tyr Gly Thr Thr Thr Gln Arg Trp Ile Asn
                405                 410                 415

Asn Asp Val Tyr Ile Tyr Glu Arg Lys Phe Phe Asn Asp Val Val Leu
                420                 425                 430

Val Ala Ile Asn Arg Asn Thr Gln Ser Ser Tyr Ser Ile Ser Gly Leu
            435                 440                 445

Gln Thr Ala Leu Pro Asn Gly Ser Tyr Ala Asp Tyr Leu Ser Gly Leu
            450                 455                 460

Leu Gly Gly Asn Gly Ile Ser Val Ser Asn Gly Ser Val Ala Ser Phe
465                 470                 475                 480

Thr Leu Ala Pro Gly Ala Val Ser Val Trp Gln Tyr Ser Thr Ser Ala
                485                 490                 495

Ser Ala Pro Gln Ile Gly Ser Val Ala Pro Asn Met Gly Ile Pro Gly
            500                 505                 510
```

-continued

```
Asn Val Val Thr Ile Asp Gly Lys Gly Phe Gly Thr Thr Gln Gly Thr
        515             520             525

Val Thr Phe Gly Gly Val Thr Ala Thr Val Lys Ser Trp Thr Ser Asn
        530             535             540

Arg Ile Glu Val Tyr Val Pro Asn Met Ala Ala Gly Leu Thr Asp Val
545             550             555             560

Lys Val Thr Ala Gly Gly Val Ser Ser Asn Leu Tyr Ser Tyr Asn Ile
                565             570             575

Leu Ser Gly Thr Gln Thr Ser Val Val Phe Thr Val Lys Ser Ala Pro
                580             585             590

Pro Thr Asn Leu Gly Asp Lys Ile Tyr Leu Thr Gly Asn Ile Pro Glu
            595             600             605

Leu Gly Asn Trp Ser Thr Asp Thr Ser Gly Ala Val Asn Asn Ala Gln
        610             615             620

Gly Pro Leu Leu Ala Pro Asn Tyr Pro Asp Trp Phe Tyr Val Phe Ser
625             630             635             640

Val Pro Ala Gly Lys Thr Ile Gln Phe Lys Phe Phe Ile Lys Arg Ala
                645             650             655

Asp Gly Thr Ile Gln Trp Glu Asn Gly Ser Asn His Val Ala Thr Thr
                660             665             670

Pro Thr Gly Ala Thr Gly Asn Ile Thr Val Thr Trp Gln Asn
        675             680             685
```

COMBINATION OF NONMALTOGENIC EXOAMYLASE AND GLUCOAMYLASE FOR IMPROVING BREAD RESILIENCE AND REDUCING AMOUNT OF ADDED SUGARS

CROSS-REFERENCE TO RELATED APPLICATIONS

This application is a U.S. National Stage Application under 35 U.S.C. § 371 of International Application No. PCT/US2021/051241, filed Sep. 21, 2021, which claims the benefit of U.S. Provisional Application No. 63/080,984, filed Sep. 21, 2020, all of which are hereby incorporated by reference in their entireties.

TECHNICAL FIELD

The present invention relates to enzymes and their use in the preparation of food. The present invention further relates to amylase enzymes and their use in preparing baked products with improved resilience.

BACKGROUND

Baked bread rapidly losses many of its fresh baked qualities. This process is known as staling. Crystallization of amylopectin takes place in starch granules days after baking, which leads to increased firmness of bread and causes bread staling. When bread stales, bread loses crumb softness and crumb moisture. As a result, crumbs become less elastic, and bread develops a leathery crust.

To counter staling, it is known in the art to incorporate anti-staling amylases into the bread dough. Enzymatic hydrolysis (by amylases, for example) of amylopectin side chains can reduce crystallization and reduce staling.

But adding anti-staling amylases to dough can have deleterious side effects. Endoamylase activity can negatively affect the quality of the final bread product by producing a sticky or gummy crumb which in turn results in a bread or crumb lacking springiness (resilience). Consumers frequently test bread softness by squeezing the packaged bread. If the bread does not spring back to its original form, consumers will have a negative perception of the bread. Springiness is also important when bread is sliced.

There is a continuing need in the art for softening (anti-staling) solutions that address the issue of bread springiness.

SUMMARY OF THE INVENTION

In accordance with an aspect of the present invention, a process is presented for making a baked product with improved resilience having the steps of adding to a dough comprising flour, water and a leavening agent, a nonmaltogenic exoamylase and a glucoamylase and baking the dough. Optionally, the nonmaltogenic exoamlyase is capable of hydrolysing starch by cleaving off one or more linear malto-oligosaccharides, predominantly consisting of from four to eight D-glucopyranosyl units, from the non-reducing ends of the side chains of amylopectin. Optionally, the non-maltogenic exoamylase has an endoamylase activity of less than 0.5 endoamylase units (EAU) per unit of exoamylase activity. Optionally, the flour is wheat flour or rye flour or mixtures thereof.

Optionally, the process has the further step of baking the dough.

In accordance with still other aspects of the preferred embodiments of the invention, the nonmaltogenic exoamylase is an enzyme having at least 70%, 80%, 85%, 90%, 95%, 98%, 99% or 100% sequence identity to SEQ ID NO:1 or a nonmaltogenic exoamylase active fragment thereof or SEQ ID NO:2 or a nonmaltogenic exoamylase active fragment thereof.

The glucoamylase is optionally an enzyme having at least 70%, 80%, 85%, 90%, 95%, 98%, 99% or 100% sequence identity to SEQ ID NO:3 or a glucoamylase active fragment thereof, SEQ ID NO:4 or a glucoamylase active fragment thereof or SEQ ID NO:5 or a glucoamylase active fragment thereof.

Optionally, the nonmaltogenic exoamylase is an enzyme having at least 70%, 80%, 85%, 90%, 95%, 98%, 99% or 100% sequence identity to SEQ ID NO:1 or a nonmaltogenic exoamylase active fragment thereof or SEQ ID NO:2 or a nonmaltogenic exoamylase active fragment thereof and the glucoamylase is an enzyme having at least 70%, 80%, 85%, 90%, 95%, 98%, 99% or 100% sequence identity to SEQ ID NO:3 or a glucoamylase active fragment thereof, SEQ ID NO:4 or a glucoamylase active fragment thereof or SEQ ID NO:5 or a glucoamylase active fragment thereof.

Optionally, the nonmaltogenic exoamylase present is in an amount from about 10 to about 100,000 Betamyl Units per Kg of flour. Optionally, the glucoamylase is present in an amount from about 10 to about 100,000 amyloglucosidase activity units (AGU) per Kg of flour. Optionally, the nonmaltogenic exoamylase is present in an amount from about 1,000 to about 90,000 Betamyl. Units per Kg of flour and the glucoamylase is present in an amount from about 1,000 to about 90,000 amyloglucosidase activity units (AGU) per Kg of flour. Optionally, the nonmaltogenic exoamylase is present in an amount from about 5,000 to about 50,000 Betamyl Units per Kg of flour and the glucoamylase is present in an amount from about 5,000 to about 50,000 amyloglucosidase activity units (AGU) per Kg of flour. Optionally, the nonmaltogenic exoamylase is present in an amount from about 1,000 to about 90,000 Betamyl Units per Kg of flour and the glucoamylase is present in an amount from about 1,000 to about 90,000 amyloglucosidase activity units (AGU) per Kg of flour.

Optionally, the nonmaltogenic exoamylase is an enzyme having at least 70%, 80%, 85%, 90%, 95%, 98%, 99% or 100% sequence identity to SEQ ID NO:1 or a nonmaltogenic exoamylase active fragment thereof and is present in an amount from about 15,000 to about 40,000 Betamyl Units and the glucoamylase is an enzyme having at least 70%, 80%, 85%, 90%, 95%, 98%, 99% or 100% sequence identity to SEQ ID NO:3 or a glucoamylase active fragment thereof and is present in an amount from about 5,000 to about 10,000 amyloglucosidase activity units (AGU) per Kg of flour.

Optionally, the nonmaltogenic exoamylase is an enzyme having at least 70%, 80%, 85%, 90%, 95%, 98%, 99% or 100% sequence identity to SEQ ID NO:2 or a nonmaltogenic exoamylase active fragment thereof and is present in an amount from about 15,000 to about 40,000 Betamyl Units and the glucoamylase is an enzyme having at least 70%, 80%, 85%, 90%, 95%, 98%, 99% or 100% sequence identity to SEQ ID NO:3 or a glucoamylase active fragment thereof and is present in an amount from about 5,000 to about 10,000 amyloglucosidase activity units (AGU) per Kg of flour.

Optionally, the nonmaltogenic exoamylase is an enzyme having at least 70%, 80%, 85%, 90%, 95%, 98%, 99% or 100% sequence identity to SEQ ID NO:1 of a nonmaltogenic exoamylase fragment thereof or SEQ ID NO:2 or a nonmaltogenic exoamylase active fragment thereof and is present in an amount from about 15,000 to about 40,000 Betamyl Units and the glucoamylase is an enzyme having at least 70%, 80%, 85%, 90%, 95%, 98%, 99% or 100% sequence identity to SEQ ID NO:4 or a glucoamylase active fragment thereof, or SEQ ID NO:5 or a glucoamylase active fragment thereof and is present in an amount from about 5,000 to about 10,000 amyloglucosidase activity units (AGU) per Kg of flour.

Optionally, a third enzyme is added to the dough selected from the group of consisting of oxidoreductases, hydrolases, lipases, esterases, glycosidases, amylases, maltogenic alpha-amylases, pullulanases, xylanases, cellulases, hemicellu-lases, starch degrading enzymes, proteases and lipoxy-genases. Optionally, the third enzyme is a maltogenic alpha-amylase.

In another aspect of the present invention, a bakery product is presented which is obtained by the process described above.

In another aspect of the present invention, a use is presented in which a non-maltogenic exoamylase and a glucoamylase in a bakery product to retard the staling of the bakery product.

In yet another aspect of the present invention, an improver composition for a dough is presented having a non-malto-genic exoamylase, a glucoamylase and at least one further dough ingredient or dough additive. Optionally, the improver composition also has a maltogenic alpha-amylase.

According to yet another aspect of the present invention a dough is presented having a non-maltogenic exoamylase and a glucoamylase. Optionally, the nonmaltogenic exoam-lyase is capable of hydrolysing starch by cleaving off one or more linear malto-oligosaccharides, predominantly consist-ing of from four to eight D-glucopyranosyl units, from the non-reducing ends of the side chains of amylopectin. Optionally, the non-maltogenic exoamylase has an endo-amylase activity of less than 0.5 endoamylase units (EAU) per unit of exoamylase activity. Preferably, the dough ingre-dient is wheat flour or rye flour or mixtures thereof.

Preferably, the nonmaltogenic exoamylase is an enzyme having at least 70%, 80%, 85%, 90%, 95%, 98%, 99% or 100% sequence identity to SEQ ID NO:1 or a nonmalto-genic exoamylase active fragment thereof or SEQ ID NO:2 or a nonmaltogenic exoamylase active fragment thereof.

Preferably, the glucoamylase is an enzyme having at least 70%, 80%, 85%, 90%, 95%, 98%, 99% or 100% sequence identity to SEQ ID NO:3 or a glucoamylase active fragment thereof, SEQ ID NO:4 or a glucoamylase active fragment thereof or SEQ ID NO:5 or a glucoamylase active fragment thereof.

Optionally, the nonmaltogenic exoamylase is an enzyme having at least 70%, 80%, 85%, 90%, 95%, 98%, 99% or 100% sequence identity to SEQ ID NO:1 or a nonmalto-genic exoamylase active fragment thereof or SEQ ID NO:2 or a nonmaltogenic exoamylase active fragment thereof and the glucoamylase is preferably an enzyme having at least 70%, 80%, 85%, 90%, 95%, 98%, 99% or 100% sequence identity to SEQ ID NO:3 or a glucoamylase active fragment thereof, SEQ ID NO:4 or a glucoamylase active fragment thereof or SEQ ID NO:5 or a glucoamylase active fragment thereof.

Optionally, the nonmaltogenic exoamylase present is in an amount from about 10 to about 100,000 Betamyl Units per Kg of flour.

Optionally, the glucoamylase is present in an amount from about 10 to about 100,000 amyloglucosidase activity units (AGU) per Kg of flour.

Optionally, the nonmaltogenic exoamylase is present in an amount from about 10 to about 100,000 Betamyl Units per Kg of flour and the glucoamylase is present in an amount from about 10 to about 100,000 amyloglucosidase activity units (AGU) per Kg of flour. Optionally, the nonmaltogenic exoamylase is present in an amount from about 1,000 to about 90,000 Betamyl Units per Kg of flour and the glu-coamylase is present in an amount from about 1,000 to about 90,000 amyloglucosidase activity units (AGU) per Kg of flour. Optionally, the nonmaltogenic exoamylase is present in an amount from about 5,000 to about 50,000 Betamyl Units per Kg of flour and the glucoamylase is present in an amount from about 5,000 to about 50,000 amyloglucosidase activity units (AGU) per Kg of flour.

Optionally, the nonmaltogenic exoamylase is an enzyme having at least 70%, 80%, 85%, 90%, 95%, 98%, 99% or 100% sequence identity to SEQ ID NO:1 or a nonmalto-genic exoamylase active fragment thereof and is present in an amount from about 15,000 to about 40,000 Betamyl Units and the glucoamylase is an enzyme having at least 70%, 80%, 85%, 90%, 95%, 98%, 99% or 100% sequence identity to SEQ ID NO:3 and is present in an amount from about 5,000 to about 10,000 amyloglucosidase activity units (AGU) per Kg of flour.

Optionally, the nonmaltogenic exoamylase is an enzyme having at least 70%, 80%, 85%, 90%, 95%, 98%, 99% or 100% sequence identity to SEQ ID NO:2 or a nonmalto-genic exoamylase active fragment thereof and is present in an amount from about 15,000 to about 40,000 Betamyl Units and the glucoamylase is an enzyme having at least 70%, 80%, 85%, 90%, 95%, 98%, 99% or 100% sequence identity to SEQ ID NO:3 and is present in an amount from about 5,000 to about 10,000 amyloglucosidase activity units (AGU) per Kg of flour.

Optionally, the dough has a third enzyme selected from the group of consisting of oxidoreductases, hydrolases, lipases, esterases, glycosidases, amylases, maltogenic alpha-amylases, pullulanases, xylanases, cellulases, hemicellu-lases, starch degrading enzymes, proteases and lipoxy-genases. Optionally, the third enzyme is a maltogenic alpha-amylase.

Optionally, the dough is baked.

BRIEF DESCRIPTION OF THE BIOLOGICAL SEQUENCES

SEQ ID NO:1 sets forth the protein sequence of the mature G4 alpha amylase variant 1 from *Pseudomonas saccharophila* (PsAA_1).

SEQ ID NO:2 sets forth the protein sequence of the mature G4 alpha amylase variant 2 from *Pseudomonas saccharophila* (PsAA_2).

SEQ ID NO:3 sets forth the protein sequence of the mature glucoamylase from *Penicillium* sp. (PspGA1).

SEQ ID NO:4 sets forth the protein sequence of the mature glucoamylase from *Rasamsonia emersonii* (ReGA1).

SEQ ID NO:5 sets forth the protein sequence of the mature glucoamylase from *Trichoderma reesei* (TrGA).

DETAILED DESCRIPTION

The practice of the present teachings will employ, unless otherwise indicated, conventional techniques of molecular biology (including recombinant techniques), microbiology, cell biology, and biochemistry, which are within the skill of the art. Such techniques are explained fully in the literature, for example, *Molecular Cloning: A Laboratory Manual*, second edition (Sambrook et al., 1989); *Oligonucleotide Synthesis* (M. J. Gait, ed., 1984; *Current Protocols in Molecular Biology* (F. M. Ausubel et al., eds., 1994); *PCR: The Polymerase Chain Reaction* (Mullis et al., eds., 1994); *Gene Transfer and Expression: A Laboratory Manual* (Kriegler, 1990), and *The Alcohol Textbook* (Ingledew et al., eds., Fifth Edition, 2009), and *Essentials of Carbohydrate Chemistry and Biochemistry* (Lindhorste, 2007).

Unless defined otherwise herein, all technical and scientific terms used herein have the same meaning as commonly understood by one of ordinary skill in the art to which the present teachings belong. Singleton, et al., *Dictionary of Microbiology and Molecular Biology*, second ed., John Wiley and Sons, New York (1994), and Hale & Markham, *The Harper Collins Dictionary of Biology*, Harper Perennial, NY (1991) provide one of skill with a general dictionary of many of the terms used in this invention. Any methods and materials similar or equivalent to those described herein can be used in the practice or testing of the present teachings.

Numeric ranges provided herein are inclusive of the numbers defining the range.

The terms, "wild-type," "parental," or "reference," with respect to a polypeptide, refer to a naturally-occurring polypeptide that does not include a man-made substitution, insertion, or deletion at one or more amino acid positions. Similarly, the terms "wild-type," "parental," or "reference," with respect to a polynucleotide, refer to a naturally-occurring polynucleotide that does not include a man-made nucleoside change. However, note that a polynucleotide encoding a wild-type, parental, or reference polypeptide is not limited to a naturally-occurring polynucleotide, and encompasses any polynucleotide encoding the wild-type, parental, or reference polypeptide.

Reference to the wild-type polypeptide is understood to include the mature form of the polypeptide. A "mature" polypeptide or variant, thereof, is one in which a signal sequence is absent, for example, cleaved from an immature form of the polypeptide during or following expression of the polypeptide.

The term "variant," with respect to a polypeptide, refers to a polypeptide that differs from a specified wild-type, parental, or reference polypeptide in that it includes one or more naturally-occurring or man-made substitutions, insertions, or deletions of an amino acid. Similarly, the term "variant," with respect to a polynucleotide, refers to a polynucleotide that differs in nucleotide sequence from a specified wild-type, parental, or reference polynucleotide. The identity of the wild-type, parental, or reference polypeptide or polynucleotide will be apparent from context.

The term "recombinant," when used in reference to a subject cell, nucleic acid, protein or vector, indicates that the subject has been modified from its native state. Thus, for example, recombinant cells express genes that are not found within the native (non-recombinant) form of the cell, or express native genes at different levels or under different conditions than found in nature. Recombinant nucleic acids differ from a native sequence by one or more nucleotides and/or are operably linked to heterologous sequences, e.g., a heterologous promoter in an expression vector. Recombinant proteins may differ from a native sequence by one or more amino acids and/or are fused with heterologous sequences. A vector comprising a nucleic acid encoding an enzyme is a recombinant vector.

The terms "recovered," "isolated," and "separated," refer to a compound, protein (polypeptides), cell, nucleic acid, amino acid, or other specified material or component that is removed from at least one other material or component with which it is naturally associated as found in nature. An "isolated" polypeptide, thereof, includes, but is not limited to, a culture broth containing secreted polypeptide expressed in a heterologous host cell.

The term "purified" refers to material (e.g., an isolated polypeptide or polynucleotide) that is in a relatively pure state, e.g., at least about 90% pure, at least about 95% pure, at least about 98% pure, or even at least about 99% pure.

The term "enriched" refers to material (e.g., an isolated polypeptide or polynucleotide) that is in about 50% pure, at least about 60% pure, at least about 70% pure, or even at least about 70% pure.

A "pH range," with reference to an enzyme, refers to the range of pH values under which the enzyme exhibits catalytic activity.

The terms "pH stable" and "pH stability," with reference to an enzyme, relate to the ability of the enzyme to retain activity over a wide range of pH values for a predetermined period of time (e.g., 15 min., 30 min., 1 hour).

The term "amino acid sequence" is synonymous with the terms "polypeptide," "protein," and "peptide," and are used interchangeably. Where such amino acid sequences exhibit activity, they may be referred to as an "enzyme." The conventional one-letter or three-letter codes for amino acid residues are used, with amino acid sequences being presented in the standard amino-to-carboxy terminal orientation (i.e., N→C).

The term "nucleic acid" encompasses DNA, RNA, heteroduplexes, and synthetic molecules capable of encoding a polypeptide. Nucleic acids may be single stranded or double stranded, and may be chemical modifications. The terms "nucleic acid" and "polynucleotide" are used interchangeably. Because the genetic code is degenerate, more than one codon may be used to encode a particular amino acid, and the present compositions and methods encompass nucleotide sequences that encode a particular amino acid sequence. Unless otherwise indicated, nucleic acid sequences are presented in 5'-to-3' orientation.

"Hybridization" refers to the process by which one strand of nucleic acid forms a duplex with, i.e., base pairs with, a complementary strand, as occurs during blot hybridization techniques and PCR techniques. Stringent hybridization conditions are exemplified by hybridization under the following conditions: 65° C. and 0.1×SSC (where 1×SSC=0.15 M NaCl, 0.015 M Na$_3$ citrate, pH 7.0). Hybridized, duplex nucleic acids are characterized by a melting temperature (T$_m$), where one half of the hybridized nucleic acids are unpaired with the complementary strand. Mismatched nucleotides within the duplex lower the T$_m$. Very stringent hybridization conditions involve 68° C. and 0.1×SSC.

A "synthetic" molecule is produced by in vitro chemical or enzymatic synthesis rather than by an organism.

The terms "transformed," "stably transformed," and "transgenic," used with reference to a cell means that the cell contains a non-native (e.g., heterologous) nucleic acid sequence integrated into its genome or carried as an episome that is maintained through multiple generations.

The term "introduced" in the context of inserting a nucleic acid sequence into a cell, means "transfection", "transformation" or "transduction," as known in the art.

A "host strain" or "host cell" is an organism into which an expression vector, phage, virus, or other DNA construct, including a polynucleotide encoding a polypeptide of interest (e.g., an enzyme) has been introduced. Exemplary host strains are microorganism cells (e.g., bacteria, filamentous fungi, and yeast) capable of expressing the polypeptide of interest. The term "host cell" includes protoplasts created from cells.

The term "heterologous" with reference to a polynucleotide or protein refers to a polynucleotide or protein that does not naturally occur in a host cell.

The term "endogenous" with reference to a polynucleotide or protein refers to a polynucleotide or protein that occurs naturally in the host cell.

The term "expression" refers to the process by which a polypeptide is produced based on a nucleic acid sequence. The process includes both transcription and translation.

A "selective marker" or "selectable marker" refers to a gene capable of being expressed in a host to facilitate selection of host cells carrying the gene. Examples of selectable markers include but are not limited to antimicrobials (e.g., hygromycin, bleomycin, or chloramphenicol) and/or genes that confer a metabolic advantage, such as a nutritional advantage on the host cell.

A "vector" refers to a polynucleotide sequence designed to introduce nucleic acids into one or more cell types. Vectors include cloning vectors, expression vectors, shuttle vectors, plasmids, phage particles, cassettes and the like.

An "expression vector" refers to a DNA construct comprising a DNA sequence encoding a polypeptide of interest, which coding sequence is operably linked to a suitable control sequence capable of effecting expression of the DNA in a suitable host. Such control sequences may include a promoter to effect transcription, an optional operator sequence to control transcription, a sequence encoding suitable ribosome binding sites on the mRNA, enhancers and sequences which control termination of transcription and translation.

The term "operably linked" means that specified components are in a relationship (including but not limited to juxtaposition) permitting them to function in an intended manner. For example, a regulatory sequence is operably linked to a coding sequence such that expression of the coding sequence is under control of the regulatory sequences.

A "signal sequence" is a sequence of amino acids attached to the N-terminal portion of a protein, which facilitates the secretion of the protein outside the cell. The mature form of an extracellular protein lacks the signal sequence, which is cleaved off during the secretion process.

"Biologically active" refers to a sequence having a specified biological activity, such an enzymatic activity.

The term "specific activity" refers to the number of moles of substrate that can be converted to product by an enzyme or enzyme preparation per unit time under specific conditions. Specific activity is generally expressed as units (U)/mg of protein. Alternatively, specific activity can refer to the number of moles of product generated by an enzyme or enzyme preparation per unit of time under specific conditions.

As used herein, "percent sequence identity" means that a particular sequence has at least a certain percentage of amino acid residues identical to those in a specified reference sequence, when aligned using the CLUSTAL W algorithm with default parameters. See Thompson et al. (1994) *Nucleic Acids Res.* 22:4673-4680. Default parameters for the CLUSTAL W algorithm are:

| Gap opening penalty: | 10.0 |
| Gap extension penalty: | 0.05 |

8

-continued

| Protein weight matrix: | BLOSUM series |
| DNA weight matrix: | IUB |
| Delay divergent sequences %: | 40 |
| Gap separation distance: | 8 |
| DNA transitions weight: | 0.50 |
| List hydrophilic residues: | GPSNDQEKR |
| Use negative matrix: | OFF |
| Toggle Residue specific penalties: | ON |
| Toggle hydrophilic penalties: | ON |
| Toggle end gap separation penalty: | OFF |

Deletions are counted as non-identical residues, compared to a reference sequence. Deletions occurring at either terminus are included. For example, a variant with five amino acid deletions of the C-terminus of the mature 617 residue polypeptide would have a percent sequence identity of 99% (612/617 identical residues×100, rounded to the nearest whole number) relative to the mature polypeptide. Such a variant would be encompassed by a variant having "at least 99% sequence identity" to a mature polypeptide.

"Fused" polypeptide sequences are connected, i.e., operably linked, via a peptide bond between two subject polypeptide sequences.

The term "filamentous fungi" refers to all filamentous forms of the subdivision Eumycotina, particularly *Pezizomycotina* species.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−10% or less, preferably +1-5% or less, more preferably +/−1% or less, and still more preferably +/−0.1% or less of and from the specified value, insofar such variations are appropriate to perform in the disclosed invention. It is to be understood that the value to which the modifier "about" or "approximately" refers is itself also specifically, and preferably, disclosed.

The term glucoamylase (GA), also known as amyloglucosidase (AMG) or g-amylase (EC 3.2.1.3), is a biocatalyst capable of hydrolyzing primarily α-1,4 glycosidic linkages (but also α-1,6 glycosidic linkages) in raw (sparsely soluble) or soluble starches and related poly- and oligosaccharides from the non-reducing end(s) in a stepwise manner to produce β-D-glucose.

The term "maltogenic alpha-amylase" (glucan 1,4-alpha-maltohydrolase, E.C. 3.2.1.133) is a biocatalyst capable of hydrolyzing amylose and amylopectin to maltose in the alpha-configuration.

The term "amylase" means an enzyme that is, among other things, capable of catalyzing the degradation of starch. An endo-acting amylase activity cleaves α-D-(1→4) O-glycosidic linkages within the starch molecule in a random fashion. In contrast, an exo-acting amylolytic activity cleaves a starch molecule from the non-reducing end of the substrate. "Endo-acting amylase activity," "endo-activity," "endo-specific activity," and "endo-specificity" are synonymous, when the terms refer to the variant polypeptides as defined in the claims. The same is true for the corresponding terms for exo-activity.

"maltotetraose-forming maltotetrahydrolase; EC 3.2.1.60; G4-forming amylase; G4-amylase and glucan 1,4-alpha-maltotetrahydrolase" may be used interchangeably".

"Resilience" is defined as the ability of a baked good such as bread to absorb energy when it is deformed elastically (for example squeezed or subjected to some other force) and to release that energy upon unloading. Bread's resilience is its ability to spring back, returning to its original shape when subjected to a compressing force.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any>3, >4, >5, >6 or >7 etc. of said members, and up to all said members.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

Additional Mutations

In some embodiments, the present enzymes further include one or more mutations that provide a further performance or stability benefit. Exemplary performance benefits include but are not limited to increased thermal stability, increased storage stability, increased solubility, an altered pH profile, increased specific activity, modified substrate specificity, modified substrate binding, modified pH-dependent activity, modified pH-dependent stability, increased oxidative stability, and increased expression. In some cases, the performance benefit is realized at a relatively low temperature. In some cases, the performance benefit is realized at relatively high temperature.

Furthermore, the present enzymes may include any number of conservative amino acid substitutions. Exemplary conservative amino acid substitutions are listed in Table 1.

TABLE 1

| Conservative amino acid substitutions | | |
| --- | --- | --- |
| For Amino Acid | Code | Replace with any of |
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, b-Ala, Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |

TABLE 1-continued

| Conservative amino acid substitutions | | |
| --- | --- | --- |
| For Amino Acid | Code | Replace with any of |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

The reader will appreciate that some of the above mentioned conservative mutations can be produced by genetic manipulation, while others are produced by introducing synthetic amino acids into a polypeptide by genetic or other means.

The present enzyme may be "precursor," "immature," or "full-length," in which case they include a signal sequence, or "mature," in which case they lack a signal sequence and may be further truncated at the N- and/or C-terminus by proteolytic and/or non-proteolytic processing. In general, the mature forms of the polypeptides are generally the most useful. Unless otherwise noted, the amino acid residue numbering used herein refers to the mature forms of the respective enzyme polypeptides. The present enzyme polypeptides may also be truncated to remove the N or C-termini, so long as the resulting polypeptides retain enzyme activity. In addition, enzymes may be active fragments derived from a longer amino acid sequence. Active fragments are characterized by retaining some or all of the activity of the full length enzyme but have deletions from the N-terminus, from the C-terminus or internally or combinations thereof.

The present enzyme may be a "chimeric" or "hybrid" polypeptide, in that it includes at least a portion of a first enzyme polypeptide, and at least a portion of a second enzyme polypeptide. The present enzyme may further include heterologous signal sequence, an epitope to allow tracking or purification, or the like. Exemplary heterologous signal sequences are from B. licheniformis amylase (LAT), B. subtilis (AmyE or AprE), and Streptomyces CelA.

Production of Enzymes

The present enzyme can be produced in host cells, for example, by secretion or intracellular expression. A cultured cell material (e.g., a whole-cell broth) comprising an enzyme can be obtained following secretion of the enzyme into the cell medium. Optionally, the enzyme can be isolated from the host cells, or even isolated from the cell broth, depending on the desired purity of the final enzyme. A gene encoding an enzyme can be cloned and expressed according to methods well known in the art. Suitable host cells include bacterial, fungal (including yeast and filamentous fungi), and plant cells (including algae). Particularly useful host cells include Aspergillus niger, Aspergillus oryzae or Trichoderma reesei. Other host cells include bacterial cells, e.g., Bacillus subtilis or B. licheniformis, as well as Streptomyces, E. Coli.

The host cell further may express a nucleic acid encoding a homologous or heterologous enzyme, i.e., a enzyme that is not the same species as the host cell, or one or more other enzymes. The enzyme may be a variant enzyme. Additionally, the host may express one or more accessory enzymes, proteins, peptides.

Vectors

A DNA construct comprising a nucleic acid encoding an enzyme can be constructed to be expressed in a host cell. Because of the well-known degeneracy in the genetic code, variant polynucleotides that encode an identical amino acid sequence can be designed and made with routine skill. It is also well-known in the art to optimize codon use for a particular host cell. Nucleic acids encoding enzyme can be incorporated into a vector. Vectors can be transferred to a host cell using well-known transformation techniques, such as those disclosed below.

The vector may be any vector that can be transformed into and replicated within a host cell. For example, a vector comprising a nucleic acid encoding an enzyme can be transformed and replicated in a bacterial host cell as a means of propagating and amplifying the vector. The vector also may be transformed into an expression host, so that the encoding nucleic acids can be expressed as a functional enzyme. Host cells that serve as expression hosts can include filamentous fungi, for example. The Fungal Genetics Stock Center (FGSC) Catalogue of Strains lists suitable vectors fr expression in fungal host cells. See FGSC, Catalogue of Strains, University of Missouri, at www.fgsc.net (last modified Jan. 17, 2007). A representative vector is pJG153, a promoterless Cre expression vector that can be replicated in a bacterial host. See Harrison et al. (June 2011) *Applied Environ. Microbiol.* 77:3916-22. pJG153 can be modified with routine skill to comprise and express a nucleic acid encoding an enzyme.

A nucleic acid encoding an enzyme can be operably linked to a suitable promoter, which allows transcription in the host cell. The promoter may be any DNA sequence that shows transcriptional activity in the host cell of choice and may be derived from genes encoding proteins either homologous or heterologous to the host cell. Exemplary promoters for directing the transcription of the DNA sequence encoding an enzyme, especially in a bacterial host, are the promoter of the lac operon of *E. coli*, the *Streptomyces coelicolor* agarase gene dagA or celA promoters, the promoters of the *Bacillus licheniformis* α-amylase gene (amyL), the promoters of the *Bacillus stearothermophilus* maltogenic amylase gene (amyM), the promoters of the *Bacillus amyloliquefaciens* α-amylase (amyQ), the promoters of the *Bacillus subtilis* xylA and xylB genes etc. For transcription in a fungal host, examples of useful promoters are those derived from the gene encoding *Aspergillus oryzae* TAKA amylase, *Rhizomucor miehei* aspartic proteinase, *Aspergillus niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase, or *A. nidulans* acetamidase. When a gene encoding an enzyme is expressed in a bacterial species such as *E. coli*, a suitable promoter can be selected, for example, from a bacteriophage promoter including a T7 promoter and a phage lambda promoter. Examples of suitable promoters for the expression in a yeast species include but are not limited to the Gal 1 and Gal 10 promoters of *Saccharomyces cerevisiae* and the *Pichia pastoris* AOX1 or AOX2 promoters. cbh1 is an endogenous, inducible promoter from *Trichoderma reesei*. See Liu et al. (2008) "Improved heterologous gene expression in *Trichoderma reesei* by cellobiohydrolase I gene (cbh1) promoter optimization," *Acta Biochim. Biophys. Sin* (Shanghai) 40(2):158-65.

The coding sequence can be operably linked to a signal sequence. The DNA encoding the signal sequence may be the DNA sequence naturally associated with the enzyme gene to be expressed or from a different Genus or species. A signal sequence and a promoter sequence comprising a DNA construct or vector can be introduced into a fungal host cell and can be derived from the same source. For example, the signal sequence is the cbh1 signal sequence that is operably linked to a cbh1 promoter.

An expression vector may also comprise a suitable transcription terminator and, in eukaryotes, polyadenylation sequences operably linked to the DNA sequence encoding a variant enzyme. Termination and polyadenylation sequences may suitably be derived from the same sources as the promoter.

The vector may further comprise a DNA sequence enabling the vector to replicate in the host cell. Examples of such sequences are the origins of replication of plasmids pUC19, pACYC177, pUB110, pE194, pAMB1, and pIJ702.

The vector may also comprise a selectable marker, e.g., a gene the product of which complements a defect in the isolated host cell, such as the dal genes from *B. subtilis* or *B. licheniformis*, or a gene that confers antibiotic resistance such as, e.g., ampicillin, kanamycin, chloramphenicol or tetracycline resistance. Furthermore, the vector may comprise *Aspergillus* selection markers such as amdS, argB, niaD and xxsC, a marker giving rise to hygromycin resistance, or the selection may be accomplished by co-transformation, such as known in the art. See e.g., International PCT Application WO 91/17243.

Intracellular expression may be advantageous in some respects, e.g., when using certain bacteria or fungi as host cells to produce large amounts of enzyme for subsequent enrichment or purification. Extracellular secretion of enzyme into the culture medium can also be used to make a cultured cell material comprising the isolated enzyme.

The expression vector typically includes the components of a cloning vector, such as, for example, an element that permits autonomous replication of the vector in the selected host organism and one or more phenotypically detectable markers for selection purposes. The expression vector normally comprises control nucleotide sequences such as a promoter, operator, ribosome binding site, translation initiation signal and optionally, a repressor gene or one or more activator genes. Additionally, the expression vector may comprise a sequence coding for an amino acid sequence capable of targeting the enzyme to a host cell organelle such as a peroxisome, or to a particular host cell compartment. Such a targeting sequence includes but is not limited to the sequence, SKL. For expression under the direction of control sequences, the nucleic acid sequence of the enzyme is operably linked to the control sequences in proper manner with respect to expression.

The procedures used to ligate the DNA construct encoding an enzyme, the promoter, terminator and other elements, respectively, and to insert them into suitable vectors containing the information necessary for replication, are well known to persons skilled in the art (see, e.g., Sambrook et al., MOLECULAR CLONING: A LABORATORY MANUAL, 2$^{nd}$ ed., Cold Spring Harbor, 1989, and 3$^{rd}$ ed., 2001).

Transformation and Culture of Host Cells

An isolated cell, either comprising a DNA construct or an expression vector, is advantageously used as a host cell in the recombinant production of an enzyme. The cell may be transformed with the DNA construct encoding the enzyme, conveniently by integrating the DNA construct (in one or more copies) in the host chromosome. This integration is generally considered to be an advantage, as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described above in connection with the different types of host cells.

Examples of suitable bacterial host organisms are Gram positive bacterial species such as *Bacillaceae* including *Bacillus subtilis, Bacillus licheniformis, Bacillus lentus, Bacillus brevis, Geobacillus* (formerly *Bacillus) stearothermophilus, Bacillus alkalophilus, Bacillus amyloliquefaciens, Bacillus coagulans, Bacillus lautus, Bacillus megaterium,* and *Bacillus thuringiensis; Streptomyces* species such as *Streptomyces murinus*; lactic acid bacterial species including *Lactococcus* sp. such as *Lactococcus lactis; Lactobacillus* sp. including *Lactobacillus reuteri; Leuconostoc* sp.; *Pediococcus* sp.; and *Streptococcus* sp. Alternatively, strains of a Gram negative bacterial species belonging to *Enterobacteriaceae* including *E. coli*, or to *Pseudomonadaceae* can be selected as the host organism.

A suitable yeast host organism can be selected from the biotechnologically relevant yeasts species such as but not limited to yeast species such as *Pichia* sp., *Hansenula* sp., or *Kluyveromyces, Yarrowinia, Schizosaccharomyces* species or a species of *Saccharomyces*, including *Saccharomyces cerevisiae* or a species belonging to *Schizosaccharomyces* such as, for example, *S. pombe* species. A strain of the methylotrophic yeast species, *Pichia pastoris*, can be used as the host organism. Alternatively, the host organism can be a *Hansenula* species. Suitable host organisms among filamentous fungi include species of *Aspergillus*, e.g., *Aspergillus niger, Aspergillus oryzae, Aspergillus tubigensis, Aspergillus awamori*, or *Aspergillus nidulans*. Alternatively, strains of a *Fusarium* species, e.g., *Fusarium oxysporum* or of a *Rhizomucor* species such as *Rhizomucor miehei* can be used as the host organism. Other suitable strains include *Thermomyces* and *Mucor* species. In addition, *Trichoderma* sp. can be used as a host. A suitable procedure for transformation of *Aspergillus* host cells includes, for example, that described in EP 238023. An enzyme expressed by a fungal host cell can be glycosylated, i.e., will comprise a glycosyl moiety. The glycosylation pattern can be the same or different as present in the wild-type enzyme. The type and/or degree of glycosylation may impart changes in enzymatic and/or biochemical properties.

It may be advantageous to delete genes from expression hosts, where the gene deficiency can be cured by the transformed expression vector. Known methods may be used to obtain a fungal host cell having one or more inactivated genes. Gene inactivation may be accomplished by complete or partial deletion, by insertional inactivation or by any other means that renders a gene nonfunctional for its intended purpose, such that the gene is prevented from expression of a functional protein. Any gene from a *Trichoderma* sp. or other filamentous fungal host that has been cloned can be deleted, for example, cbh1, cbh2, egl1, and egl2 genes. Gene deletion may be accomplished by inserting a form of the desired gene to be inactivated into a plasmid by methods known in the art.

Introduction of a DNA construct or vector into a host cell includes techniques such as transformation; electroporation; nuclear microinjection; transduction; transfection, e.g., lipofection mediated and DEAE-Dextrin mediated transfection; incubation with calcium phosphate DNA precipitate; high velocity bombardment with DNA-coated microprojectiles; and protoplast fusion. General transformation techniques are known in the art. See, e.g., Sambrook et al. (2001), supra. The expression of heterologous protein in *Trichoderma* is described, for example, in U.S. Pat. No. 6,022,725. Reference is also made to Cao et al. (2000) *Science* 9:991-1001 for transformation of *Aspergillus* strains. Genetically stable transformants can be constructed with vector systems whereby the nucleic acid encoding an enzyme is stably integrated into a host cell chromosome. Transformants are then selected and purified by known techniques.

The preparation of *Trichoderma* sp. for transformation, for example, may involve the preparation of protoplasts from fungal mycelia. See Campbell et al. (1989) *Curr. Genet.* 16:53-56. The mycelia can be obtained from germinated vegetative spores. The mycelia are treated with an enzyme that digests the cell wall, resulting in protoplasts. The protoplasts are protected by the presence of an osmotic stabilizer in the suspending medium. These stabilizers include sorbitol, mannitol, potassium chloride, magnesium sulfate, and the like. Usually the concentration of these stabilizers varies between 0.8 M and 1.2 M, e.g., a 1.2 M solution of sorbitol can be used in the suspension medium.

Uptake of DNA into the host *Trichoderma* sp. strain depends upon the calcium ion concentration. Generally, between about 10-50 mM $CaCl_2$ is used in an uptake solution. Additional suitable compounds include a buffering system, such as TE buffer (10 mM Tris, pH 7.4; 1 mM EDTA) or 10 mM MOPS, pH 6.0 and polyethylene glycol. The polyethylene glycol is believed to fuse the cell membranes, thus permitting the contents of the medium to be delivered into the cytoplasm of the *Trichoderma* sp. strain. This fusion frequently leaves multiple copies of the plasmid DNA integrated into the host chromosome.

Usually transformation of *Trichoderma* sp. uses protoplasts or cells that have been subjected to a permeability treatment, typically at a density of $10^5$ to $10^7$/mL, particularly $2\times10^6$/mL. A volume of 100 μL of these protoplasts or cells in an appropriate solution (e.g., 1.2 M sorbitol and 50 mM $CaCl_2$) may be mixed with the desired DNA. Generally, a high concentration of PEG is added to the uptake solution. From 0.1 to 1 volume of 25% PEG 4000 can be added to the protoplast suspension; however, it is useful to add about 0.25 volumes to the protoplast suspension. Additives, such as dimethyl sulfoxide, heparin, spermidine, potassium chloride and the like, may also be added to the uptake solution to facilitate transformation. Similar procedures are available for other fungal host cells. See, e.g., U.S. Pat. No. 6,022,725.

Expression

A method of producing an enzyme may comprise cultivating a host cell as described above under conditions conducive to the production of the enzyme and recovering the enzyme from the cells and/or culture medium.

The medium used to cultivate the cells may be any conventional medium suitable for growing the host cell in question and obtaining expression of an enzyme. Suitable media and media components are available from commercial suppliers or may be prepared according to published recipes (e.g., as described in catalogues of the American Type Culture Collection).

An enzyme secreted from the host cells can be used in a whole broth preparation. In the present methods, the preparation of a spent whole fermentation broth of a recombinant microorganism can be achieved using any cultivation method known in the art resulting in the expression of an enzyme. Fermentation may, therefore, be understood as comprising shake flask cultivation, small- or large-scale fermentation (including continuous, batch, fed-batch, or solid-state fermentations) in laboratory or industrial fermenters performed in a suitable medium and under conditions allowing the enzyme to be expressed or isolated. The term "spent whole fermentation broth" is defined herein as unfractionated contents of fermentation material that includes culture medium, extracellular proteins (e.g., enzymes), and cellular biomass. It is understood that the term "spent whole fermentation broth" also encompasses cellular biomass that has been lysed or permeabilized using methods well known in the art.

An enzyme secreted from the host cells may conveniently be recovered from the culture medium by well-known procedures, including separating the cells from the medium by centrifugation or filtration, and precipitating proteinaceous components of the medium by means of a salt such as ammonium sulfate, followed by the use of chromatographic procedures such as ion exchange chromatography, affinity chromatography, or the like.

The polynucleotide encoding an enzyme in a vector can be operably linked to a control sequence that is capable of providing for the expression of the coding sequence by the host cell, i.e. the vector is an expression vector. The control sequences may be modified, for example by the addition of further transcriptional regulatory elements to make the level of transcription directed by the control sequences more responsive to transcriptional modulators. The control sequences may in particular comprise promoters.

Host cells may be cultured under suitable conditions that allow expression of an enzyme. Expression of the enzymes may be constitutive such that they are continually produced, or inducible, requiring a stimulus to initiate expression. In the case of inducible expression, protein production can be initiated when required by, for example, addition of an inducer substance to the culture medium, for example dexamethasone or IPTG or Sophorose. Polypeptides can also be produced recombinantly in an in vitro cell-free system, such as the TNT™ (Promega) rabbit reticulocyte system.

An expression host also can be cultured in the appropriate medium for the host, under aerobic conditions. Shaking or a combination of agitation and aeration can be provided, with production occurring at the appropriate temperature for that host, e.g., from about 25° C. to about 75° C. (e.g., 30° C. to 45° C.), depending on the needs of the host and production of the desired enzyme. Culturing can occur from about 12 to about 100 hours or greater (and any hour value there between, e.g., from 24 to 72 hours). Typically, the culture broth is at a pH of about 4.0 to about 8.0, again depending on the culture conditions needed for the host relative to production of an enzyme.

Methods for Enriching and Purifying Enzymes

Fermentation, separation, and concentration techniques are well known in the art and conventional methods can be used in order to prepare an enzyme polypeptide-containing solution.

After fermentation, a fermentation broth is obtained, the microbial cells and various suspended solids, including residual raw fermentation materials, are removed by conventional separation techniques in order to obtain an enzyme solution. Filtration, centrifugation, microfiltration, rotary vacuum drum filtration, ultrafiltration, centrifugation followed by ultra-filtration, extraction, or chromatography, or the like, are generally used.

It is desirable to concentrate an enzyme polypeptide-containing solution in order to optimize recovery. Use of unconcentrated solutions requires increased incubation time in order to collect the enriched or purified enzyme precipitate.

The enzyme containing solution is concentrated using conventional concentration techniques until the desired enzyme level is obtained. Concentration of the enzyme containing solution may be achieved by any of the techniques discussed herein. Exemplary methods of enrichment and purification include but are not limited to rotary vacuum filtration and/or ultrafiltration.

The enzyme solution is concentrated into a concentrated enzyme solution until the enzyme activity of the concentrated enzyme polypeptide-containing solution is at a desired level.

Concentration may be performed using, e.g., a precipitation agent, such as a metal halide precipitation agent. Metal halide precipitation agents include but are not limited to alkali metal chlorides, alkali metal bromides and blends of two or more of these metal halides. Exemplary metal halides include sodium chloride, potassium chloride, sodium bromide, potassium bromide and blends of two or more of these metal halides. The metal halide precipitation agent, sodium chloride, can also be used as a preservative.

The metal halide precipitation agent is used in an amount effective to precipitate an enzyme. The selection of at least an effective amount and an optimum amount of metal halide effective to cause precipitation of the enzyme, as well as the conditions of the precipitation for maximum recovery including incubation time, pH, temperature and concentration of enzyme, will be readily apparent to one of ordinary skill in the art, after routine testing.

Generally, at least about 5% w/v (weight/volume) to about 25% w/v of metal halide is added to the concentrated enzyme solution, and usually at least 8% w/v. Generally, no more than about 25% w/v of metal halide is added to the concentrated enzyme solution and usually no more than about 20% w/v. The optimal concentration of the metal halide precipitation agent will depend, among others, on the nature of the specific enzyme polypeptide and on its concentration in the concentrated enzyme solution.

Another alternative way to precipitate the enzyme is to use organic compounds. Exemplary organic compound precipitating agents include: 4-hydroxybenzoic acid, alkali metal salts of 4-hydroxybenzoic acid, alkyl esters of 4-hydroxybenzoic acid, and blends of two or more of these organic compounds. The addition of the organic compound precipitation agents can take place prior to, simultaneously with or subsequent to the addition of the metal halide precipitation agent, and the addition of both precipitation agents, organic compound and metal halide, may be carried out sequentially or simultaneously.

Generally, the organic precipitation agents are selected from the group consisting of alkali metal salts of 4-hydroxybenzoic acid, such as sodium or potassium salts, and linear or branched alkyl esters of 4-hydroxybenzoic acid, wherein the alkyl group contains from 1 to 12 carbon atoms, and blends of two or more of these organic compounds. The organic compound precipitation agents can be, for example, linear or branched alkyl esters of 4-hydroxybenzoic acid, wherein the alkyl group contains from 1 to 10 carbon atoms, and blends of two or more of these organic compounds. Exemplary organic compounds are linear alkyl esters of 4-hydroxybenzoic acid, wherein the alkyl group contains from 1 to 6 carbon atoms, and blends of two or more of these organic compounds. Methyl esters of 4-hydroxybenzoic acid, propyl esters of 4-hydroxybenzoic acid, butyl ester of 4-hydroxybenzoic acid, ethyl ester of 4-hydroxybenzoic acid and blends of two or more of these organic compounds can also be used. Additional organic compounds also include but are not limited to 4-hydroxybenzoic acid methyl ester (named methyl PARABEN), 4-hydroxybenzoic acid propyl ester (named propyl PARABEN), which also are both preservative agents. For further descriptions, see, e.g., U.S. Pat. No. 5,281,526.

Addition of the organic compound precipitation agent provides the advantage of high flexibility of the precipitation conditions with respect to pH, temperature, enzyme concentration, precipitation agent concentration, and time of incubation.

The organic compound precipitation agent is used in an amount effective to improve precipitation of the enzyme by means of the metal halide precipitation agent. The selection of at least an effective amount and an optimum amount of organic compound precipitation agent, as well as the conditions of the precipitation for maximum recovery including incubation time, pH, temperature and concentration of enzyme, will be readily apparent to one of ordinary skill in the art, in light of the present disclosure, after routine testing.

Generally, at least about 0.01% w/v of organic compound precipitation agent is added to the concentrated enzyme solution and usually at least about 0.02% w/v. Generally, no more than about 0.3% w/v of organic compound precipitation agent is added to the concentrated enzyme solution and usually no more than about 0.2% w/v.

The concentrated polypeptide solution, containing the metal halide precipitation agent, and the organic compound precipitation agent, can be adjusted to a pH, which will, of necessity, depend on the enzyme to be enriched or purified. Generally, the pH is adjusted at a level near the isoelectric point of the enzyme. The pH can be adjusted at a pH in a range from about 2.5 pH units below the isoelectric point (pI) up to about 2.5 pH units above the isoelectric point.

The incubation time necessary to obtain an enriched or purified enzyme precipitate depends on the nature of the specific enzyme, the concentration of enzyme, and the specific precipitation agent(s) and its (their) concentration. Generally, the time effective to precipitate the enzyme is between about 1 to about 30 hours; usually it does not exceed about 25 hours. In the presence of the organic compound precipitation agent, the time of incubation can still be reduced to less about 10 hours and in most cases even about 6 hours.

Generally, the temperature during incubation is between about 4° C. and about 50° C. Usually, the method is carried out at a temperature between about 10° C. and about 45° C. (e.g., between about 20° C. and about 40° C.). The optimal temperature for inducing precipitation varies according to the solution conditions and the enzyme or precipitation agent(s) used.

The overall recovery of enriched or purified enzyme precipitate, and the efficiency with which the process is conducted, is improved by agitating the solution comprising the enzyme, the added metal halide and the added organic compound. The agitation step is done both during addition of the metal halide and the organic compound, and during the subsequent incubation period. Suitable agitation methods include mechanical stirring or shaking, vigorous aeration, or any similar technique.

After the incubation period, the enriched or purified enzyme is then separated from the dissociated pigment and other impurities and collected by conventional separation techniques, such as filtration, centrifugation, microfiltration, rotary vacuum filtration, ultrafiltration, press filtration, cross membrane microfiltration, cross flow membrane microfiltration, or the like. Further enrichment or purification of the enzyme precipitate can be obtained by washing the precipitate with water. For example, the enriched or purified enzyme precipitate is washed with water containing the metal halide precipitation agent, or with water containing the metal halide and the organic compound precipitation agents.

During fermentation, an enzyme polypeptide accumulates in the culture broth. For the isolation, enrichment, or purification of the desired enzyme, the culture broth is centrifuged or filtered to eliminate cells, and the resulting cell-free liquid is used for enzyme enrichment or purification. In one embodiment, the cell-free broth is subjected to salting out using ammonium sulfate at about 70% saturation; the 70% saturation-precipitation fraction is then dissolved in a buffer and applied to a column such as a Sephadex G-100 column, and eluted to recover the enzyme-active fraction. For further enrichment or purification, a conventional procedure such as ion exchange chromatography may be used.

Enriched or purified enzymes can be made into a final product that is either liquid (solution, slurry) or solid (granular, powder).

Exo-Specificity

It is known that some non-maltogenic exoamylases can have some degree of endoamylase activity. In some cases, this type of activity may need to be reduced or eliminated since endoamylase activity can possibly negatively effect the quality of the final bread product by producing a sticky or gummy crumb due to the accumulation of branched dextrins.

Exo-specificity can usefully be measured by determining the ratio of total amylase activity to the total endoamylase activity. This ratio is referred to in this document as a "Exo-specificity index". In preferred embodiments, an enzyme is considered an exoamylase if it has a exo-specificity index of 20 or more, i.e., its total amylase activity (including exo-amylase activity) is 20 times or more greater than its endoamylase activity. In highly preferred embodiments, the exo-specificity index of exoamylases is 30 or more, 40 or more, 50 or more, 60 or more, 70 or more, 80 or more, 90 or more, or 100 or more. In highly preferred embodiments, the exo-specificity index is 150 or more, 200 or more, 300 or more, 400 or more, 500 or more or 600 or more.

The total amylase activity and the endoamylase activity may be measured by any means known in the art. For example, the total amylase activity may be measured by assaying the total number of reducing ends released from a starch substrate. Alternatively, the use of a Betamyl assay is described in further detail in the Examples, and for convenience, amylase activity as assayed in the Examples is described in terms of "Betamyl Units" in the Tables.

Endoamylase activity may be assayed by use of a Phadebas Kit (Pharmacia and Upjohn). This makes use of a blue labelled crosslinked starch (labelled with an azo dye); only internal cuts in the starch molecule release label, while external cuts do not do so. Release of dye may be measured by spectrophotometry. Accordingly, the Phadebas Kit measures endoamylase activity, and for convenience, the results of such an assay are referred to in this document as "Phadebas units".

In a highly preferred embodiment, therefore, the exo-specificity index is expressed in terms of Betamyl Units/Phadebas Units, also referred to as "B/Phad".

Exo-specificity may also be assayed according to the methods described in the prior art, for example, in our International Patent Publication Number WO99/50399. This measures exo-specificity by way of a ratio between the endoamylase activity to the exoamylase activity. Thus, in a preferred aspect, the variant polypeptide described here will have less than 0.5 endoamylase units (EAU) per unit of exoamylase activity. Preferably the non-maltogenic exoamylases which are suitable for use according to the present invention have less than 0.05 EAU per unit of exoamylase activity and more preferably less than 0.01 EAU per unit of exoamylase activity.

DESCRIPTION OF THE PREFERRED EMBODIMENTS

In accordance with an aspect of the present invention, a process is presented for making a baked product with improved resilience having the steps of adding to a dough comprising flour, water and a leavening agent, a nonmaltogenic exoamylase and a glucoamylase and baking the dough. Preferably, the nonmaltogenic exoamlyase is capable of hydrolysing starch by cleaving off one or more linear malto-oligosaccharides, predominantly consisting of from four to eight D-glucopyranosyl units, from the non-reducing ends of the side chains of amylopectin. Preferably, the non-maltogenic exoamylase has an endoamylase activity of less than 0.5 endoamylase units (EAU) per unit of exoamylase activity. Preferably, the flour is wheat flour or rye flour or mixtures thereof.

In certain preferred embodiments, the process has the futher step of baking the dough.

In accordance with still other aspects of the preferred embodiments of the invention, the nonmaltogenic exoamylase is an enzyme having at least 70%, 80%, 85%, 90%, 95%, 98%, 99% or 100% sequence identity to SEQ ID NO:1 or a nonmaltogenic exoamylase active fragment thereof or SEQ ID NO:2 or a nonmaltogenic exoamylase active fragment thereof.

The glucoamylase is preferably an enzyme having at least 70%, 80%, 85%, 90%, 95%, 98%, 99% or 100% sequence identity to SEQ ID NO:3 or a glucoamylase active fragment thereof, SEQ ID NO:4 or a glucoamylase active fragment thereof or SEQ ID NO:5 or a glucoamylase active fragment thereof.

In a preferred embodiment of the present invention, the nonmaltogenic exoamylase is an enzyme having at least 70%, 80%, 85%, 90%, 95%, 98%, 99% or 100% sequence identity to SEQ ID NO:1 or a nonmaltogenic exoamylase active fragment thereof or SEQ ID NO:2 or a nonmaltogenic exoamylase active fragment thereof and the glucoamylase is an enzyme having at least 70%, 80%, 85%, 90%, 95%, 98%, 99% or 100% sequence identity to SEQ ID NO:3 or a glucoamylase active fragment thereof, SEQ ID NO:4 or a glucoamylase active fragment thereof or SEQ ID NO:5 or a glucoamylase active fragment thereof.

In another preferred embodiment of the present invention, the nonmaltogenic exoamylase present is in an amount from about 10 to about 100,000 Betamyl Units per Kg of flour. In still other preferred embodiment of the present invention, the glucoamylase is present in an amount from about 10 to about 100,000 amyloglucosidase activity units (AGU) per Kg of flour. More preferably, the nonmaltogenic exoamylase is present in an amount from about 10 to about 100,000 Betamyl Units per Kg of flour and the glucoamylase is present in an amount from about 10 to about 100,000 amyloglucosidase activity units (AGU) per Kg of flour. Still more preferably, the nonmaltogenic exoamylase is present in an amount from about 1,000 to about 90,000 Betamyl Units per Kg of flour and the glucoamylase is present in an amount from about 1,000 to about 90,000 amyloglucosidase activity units (AGU) per Kg of flour. Yet more preferably, the nonmaltogenic exoamylase is present in an amount from about 5,000 to about 50,000 Betamyl Units per Kg of flour and the glucoamylase is present in an amount from about 5,000 to about 50,000 amyloglucosidase activity units (AGU) per Kg of flour. In still other preferred embodiments, the nonmaltogenic exoamylase is present in an amount from about 1,000 to about 90,000 Betamyl Units per Kg of flour and the glucoamylase is present in an amount from about 1,000 to about 90,000 amyloglucosidase activity units (AGU) per Kg of flour.

In another aspect of the present invention, the nonmaltogenic exoamylase is an enzyme having at least 70%, 80%, 85%, 90%, 95%, 98%, 99% or 100% sequence identity to SEQ ID NO:1 or a nonmaltogenic exoamylase active fragment thereof and is present in an amount from about 15,000 to about 40,000 Betamyl Units and the glucoamylase is an enzyme having at least 70%, 80%, 85%, 90%, 95%, 98%, 99% or 100% sequence identity to SEQ ID NO:3 or a glucoamylase active fragment thereof and is present in an amount from about 5,000 to about 10,000 amyloglucosidase activity units (AGU) per Kg of flour.

In yet another aspect of the present invention, the nonmaltogenic exoamylase is an enzyme having at least 70%, 80%, 85%, 90%, 95%, 98%, 99% or 100% sequence identity to SEQ ID NO:2 or a nonmaltogenic exoamylase active fragment thereof and is present in an amount from about 15,000 to about 40,000 Betamyl Units and the glucoamylase is is an enzyme having at least 70%, 80%, 85%, 90%, 95%, 98%, 99% or 100% sequence identity to SEQ ID NO:3 or a glucoamylase active fragment thereof and is present in an amount from about 5,000 to about 10,000 amyloglucosidase activity units (AGU) per Kg of flour.

In yet another aspect of the present invention, the nonmaltogenic exoamylase is an enzyme having at least 70%, 80%, 85%, 90%, 95%, 98%, 99% or 100% sequence identity to SEQ ID NO:1 or a nonmaltogenic exoamylase active fragment thereof or SEQ ID NO:2 or a nonmaltogenic exoamylase active fragment thereof and is present in an amount from about 15,000 to about 40,000 Betamyl Units and the glucoamylase is is an enzyme having at least 70%, 80%, 85%, 90%, 95%, 98%, 99% or 100% sequence identity to SEQ ID NO:4 or a glucoamylase active fragment thereof or SEQ ID NO:5 or a glucoamylase active fragment thereof and is present in an amount from about 5,000 to about 10,000 amyloglucosidase activity units (AGU) per Kg of flour.

In another aspect of the present invention, a method is provided for reducing the amount of added sugar (sucrose) that it is necessary to add to bread or dough to achieve a desired level of sweetness. According to this aspect of the present invention, a process is presented for making a baked product with enhanced sweetness having the steps of adding to a dough comprising flour, water and a leavening agent, a nonmaltogenic exoamylase and a glucoamylase whereby the concentration in the dough of glucose is increased via action of the enzymes acting on the carbohydrates in the dough. The resulting increase in glucose acts to increase the sweetness of the dough. As the dough is sweeter from the glucose, less sucrose needs to be added to the dough to achieve the same level of sweetness as provided by higher levels of sucrose where the dough has less glucose.

In another aspect of the present invention, a third enzyme is added to the dough selected from the group of consisting of oxidoreductases, hydrolases, lipases, esterases, glycosidases, amylases, maltogenic alpha-amylases, pullulanases, xylanases, cellulases, hemicellulases, starch degrading enzymes, proteases and lipoxygenases. Preferably, the Bird enzyme is a maltogenic alpha-amylase.

In another aspect of the present invention a bakery product is presented which is obtained by the process described above.

In another aspect of the present invention, a use is presented in which a non-maltogenic exoamylase and a glucoamylase in a bakery product to retard the staling of the bakery product.

In yet another aspect of the present invention, an improver composition for a dough is presented having a non-malto-genic exoamylase, a glucoamylase and at least one further dough ingredient or dough additive. Preferably, the improver composition also has a maltogenic alpha-amylase.

According to yet another aspect of the present invention a dough is presented having a non-maltogenic exoamylase and a glucoamylase. Preferably, the nonmaltogenic exoam-lyase is capable of hydrolysing starch by cleaving off one or more linear malto-oligosaccharides, predominantly consist-ing of from four to eight D-glucopyranosyl units, from the non-reducing ends of the side chains of amylopectin. More preferably, the non-maltogenic exoamylase has an endoamy-lase activity of less than 0.5 endoamylase units (EAU) per unit of exoamylase activity. Preferably, the dough ingredient is wheat flour or rye flour or mixtures thereof.

Preferably, the nonmaltogenic exoamylase is an enzyme having at least 70%, 80%, 85%, 90%, 95%, 98%, 99% or 100% sequence identity to SEQ ID NO:1 or a nonmalto-genic exoamylase active fragment thereof or SEQ ID NO:2 or a nonmaltogenic exoamylase active fragment thereof.

Preferably, the glucoamylase is an enzyme having at least 70%, 80%, 85%, 90%, 95%, 98%, 99% or 100% sequence identity to SEQ ID NO:3 or a glucoamylase active fragment thereof, SEQ ID NO:4 or a glucoamylase active fragment thereof or SEQ ID NO:5 or a glucoamylase active fragment thereof.

In still more preferred embodiments, the nonmaltogenic exoamylase is an enzyme having at least 70%, 80%, 85%, 90%, 95%, 98%, 99% or 100% sequence identity to SEQ ID NO:1 or a nonmaltogenic exoamylase active fragment thereof or SEQ ID NO:2 or a nonmaltogenic exoamylase active fragment thereof and the glucoamylase is preferably an enzyme having at least 70%, 80%, 85%, 90%, 95%, 98%, 99% or 100% sequence identity to SEQ ID NO:3 or a glucoamylase active fragment thereof, SEQ ID NO:4 or a glucoamylase active fragment thereof or SEQ ID NO:5 or a glucoamylase active fragment thereof.

Preferaly, the nonmaltogenic exoamylase present is in an amount from about 10 to about 100,000 Betamyl Units per Kg of flour.

Preferably, the glucoamylase is present in an amount from about 10 to about 100,000 amyloglucosidase activity units (AGU) per Kg of flour.

Still more preferably, the nonmaltogenic exoamylase is present in an amount from about 10 to about 100,000 Betamyl Units per Kg of flour and the glucoamylase is present in an amount from about 10 to about 100,000 amyloglucosidase activity units (AGU) per Kg of flour. More preferably, the nonmaltogenic exoamylase is present in an amount from about 1,000 to about 90,000 Betamyl Units per Kg of flour and the glucoamylase is present in an amount from about 1,000 to about 90,000 amyloglucosidase activity units (AGU) per Kg of flour. Still more preferably, the nonmaltogenic exoamylase is present in an amount from about 5,000 to about 50,000 Betamyl Units per Kg of flour and the glucoamylase is present in an amount from about 5,000 to about 50,000 amyloglucosidase activity units (AGU) per Kg of flour.

In still more preferred embodiments, the nonmaltogenic exoamylase is an enzyme having at least 70%, 80%, 85%, 90%, 95%, 98%, 99% or 100% sequence identity to SEQ ID NO:1 or a nonmaltogenic exoamylase active fragment thereof and is present in an amount from about 15,000 to about 40,000 Betamyl Units and the glucoamylase is is an enzyme having at least 70%, 80%, 85%, 90%, 95%, 98%, 99% or 100% sequence identity to SEQ ID NO:3 and is present in an amount from about 5,000 to about 10,000 amyloglucosidase activity units (AGU) per Kg of flour.

Yet more preferably, the nonmaltogenic exoamylase is an enzyme having at least 70%, 80%, 85%, 90%, 95%, 98%, 99% or 100% sequence identity to SEQ ID NO:2 or a nonmaltogenic exoamylase active fragment thereof and is present in an amount from about 15,000 to about 40,000 Betamyl Units and the glucoamylase is is an enzyme having at least 70%, 80%, 85%, 90%, 95%, 98%, 99% or 100% sequence identity to SEQ ID NO:3 and is present in an amount from about 5,000 to about 10,000 amyloglucosidase activity units (AGU) per Kg of flour.

In still more preferred embodiment of the present inven-tion, the dough has a third enzyme selected from the group of consisting of oxidoreductases, hydrolases, lipases, esterases, glycosidases, amylases, maltogenic alpha-amy-lases, pullulanases, xylanases, cellulases, hemicellulases, starch degrading enzymes, proteases and lipoxygenases. Preferably, the third enzyme is a maltogenic alpha-amylase.

According to certain preferred aspects of the present invention, the dough is baked.

The invention will now be described, by way of example only, with reference to the following Examples.

Example 1. Enzymes

As an example of a G4 alpha amylase variant 1 from *Pseudomonas saccharophila* (PsAA_1) having the amino acid sequence shown in SEQ ID NO:1, GRINDAMYL CAPTIVE TS-E 1514 from DuPont was used.

As an example of a G4 alpha amylase variant 2 from *Pseudomonas saccharophila* (PsAA_2) having the amino acid sequence shown in SEQ ID NO:2, Powerfresh 8100 from DuPont was used.

PspGA: A glucoamylase from *Penicillium* sp. having the amino acid sequence shown in SEQ ID NO:3.

ReGA: A glucoamylase from *Rasamsonia emmersonii.* having the amino acid sequence shown in SEQ ID NO:4.

TrGA: A glucoamylase from *Trichoderma reesei.* having the amino acid sequence shown in SEQ ID NO:5.

Example 2. Expression and Production of Glucoamylases from *Penicillium* sp. (PspGA1) and *Rasamsonia* sp (ReGA) in *T. reesei*

The PspGA1 and ReGA glucoamylases was produced essentially using methods described in (WO2018/164737). Polynucleotide fragments corresponding to the coding sequences of PspGA1 and ReGA were synthesized by Generay (Generay Biotech Co., Ltd, Shanghai, China) using preferred codons for fungal expression host *Trichoderma reesei* (*T. reesei*). The coding sequences were inserted into a suitable *T. reesei* expression vector e.g. the pTrex3gM expression vector described in U.S. Published Application 2011/0136197 A1. The resulting expression plasmids were transformed into a suitable *T. reesei* host strain e.g. the quad-deleted *T. reesei* strain described in WO 05/001036 using a suitable method e.g. the protoplast transformation method described in (Te'o et al., J. Microbiol. Methods 51:393-99, 2002). The transformants were selected and fermented by the methods described in e.g. WO 2016/138315. Supernatants from these cultures were used to confirm GA protein expression by SDS-PAGE analysis and glucoamylase activity assays. Protein determination by OD 280 nm absorbance readings.

ReGA UFC (ultra filtration concentrate) samples were serial diluted in buffer (20 mM sodium phosphate, pH 6.0). Based on SDS-PAGE of the serial diluted UFC samples ReGA is estimated to account for 90% of the total protein present. Absorbance at 280 nm of the dilutes samples were measured in a 96 well UV MTP plate in a spectramax 384 PLUS spectrophotometer using the Softmax protein quant protocol. The molar Extinction Coefficient for the predicted mature ReGA was calculated to be: 127,700 using Geneious Prime® 2020.0.5.

The protein concentration of PspGA1 was estimated from a version of the Biuret Protein Assay method as modified by Weichselbaum and Gornall using Bovine Serum Albumin as a calibrator (modified Biuret) (Weichselbaum, Amer. J. Clin. Path. 1960, 16:40; Gornall et al., J. Biol. Chem. 1949, 177:752). Biuret reagents including calibration were purchased from Pointe Scientific Inc. US.

Example 3. Recipe and Procedure 1 for Straight Dough Baking Trials with 8% Sugar Baking trials were carried out with a standard white bread straight dough recipe for US toast. The straight dough is prepared from 2000 g of Wheat flour from Grain Craft (DK2019-00087), USA, 1220 g of tap-water, 40 g of Rapeseed Oil (Prod. No. 3520, AAK, Denmark), 160 g Sucrose, 40 g NaCl, 7 g of calcium propionate (DuPont Nutrition Bioscience, Denmark), 80 g compressed yeast (S. cerevisiae, HAGOLD HEFE, Schwarzenbach a.d. Saale, Germany) and 0.15 g ascorbic acid (DuPont Nutrition Bioscience, Denmark). The following enzymes are used beside the enzymes for anti-staling; 50 ppm GRINDAMYL® SUREBake 800 a hexose oxidase (DuPont Nutrition Bioscience, Denmark), 25 ppm GRINDAMYL™ POWERBake 950 a xylanase (DuPont Nutrition Bioscience, Denmark) and 275 ppm GRINDAMYL® A 1000 fungal alpha-amylase as target depending on the falling number of the flour (DuPont Nutrition Bioscience, Denmark).

All ingredients are mixed subsequently 2 min. at speed 2 on a Hobart A200 spiral mixer and following 18 minutes medium speed with a dough temperature of 26-27° C. The dough is afterwards scaled into 4 dough pieces at 703 g=5.11 cubic inch/oz dough pieces, rested for 5 minutes at ambient temperature and molded on a cross grain molder, Benier MS500 with the following settings: Preform: −18, Drum press.: 3, Pressure board: 4.0 cm front, 3.5 cm back, Width: 350 mm front, 320 mm back. Hereafter the dough is transferred to pans/tins and proofed for 55 min. at 43° C. with 75% RH (relative humidity) and then baked for 25 min. at 205° C. in a Reed Rack Oven. The final loaf temperature was verified to be 96-98° C. and after baking the breads were cooled for 60 minutes at ambient temperature before weighing and measuring of volume. The bread used for softness, resilience and adhesiveness measurements were packed with vacuum

Example 4. Recipe and Procedure 2 for Straight Dough Baking Trials with 8% Sugar Baking trials were carried out using a white straight pan dough in a standard format. For an 8% sugar formula, the dough was prepared using 2000 g of flour from Grain Craft (Brand Bake-Rite, Unbleached, enriched, malted), 160 g of Sucrose (Western Sugar), 80 g of compressed yeast (S.

cerevisiae, Red Star), 40 g of NaCl (Morton), 8 g of calcium propionate (Niacet), 40 g of soybean oil (Sysco), 1220 g of tap water, and 0.15 g ascorbic acid (Univar, 75 ppm based on flour weight). The following enzymes were used based on flour weight along with the enzymes for anti-staling; 50 ppm GRINDAMYL® SUREBake 800 a hexose oxidase (DuPont Nutrition & Bioscience), 50 ppm GRINDAMYL™ POWERBake 960 a xylanase and fungal alpha-amylase blend (DuPont Nutrition & Bioscience). All ingredients were mixed on a Hobart 20-Quart Globe mixer for 1 minute at speed 1, then 13 minutes at speed 2. The dough temperature after mixing was between 26-27° C. The dough was then scaled into 737 g dough pieces, rested for 5 minutes at ambient temperature, and molded and sheeted on a Stickelber cross-grain molder and sheeter. After molding, the dough was transferred into four-strapped pans and proofed at 40.5° C. with 75% RH to template at a height of ½" over the pan. The dough was baked for 26 minutes at 210° C. in a Reed Oven. The final loaf temperature was verified to be 95-98°. The bread was cooled for 60 minutes at ambient temperature before putting into plastic poly bags closed with a zip tie for storage.

Example 5. Recipe and Procedure 3 for a Lean Formula Straight Dough Baking Trials with 1% Sugar Baking trials were carried out using a white straight pan dough in a standard format. For a 1% sugar formula, the dough was prepared using 2000 g of flour from Grain Craft (Brand Bake-Rite, Unbleached, enriched, malted), 20 g of sucrose (Western Sugar), 80 g of yeast (S. cerevisiae, Red Star), 40 g of NaCl (Morton), 8 g of calcium propionate (Niacet), 40 g of soybean oil, 1160 g of water, and 0.15 g ascorbic acid (Univar, 75 ppm based on flour weight). The following enzymes were used based on flour weight along with the enzymes for anti-staling; 50 ppm GRINDAMYL® SUREBake 800 a hexose oxidase (DuPont Nutrition & Bioscience), 50 ppm GRINDAMYL™ POWERBake 960 a xylanase and fungal alpha-amylase blend (DuPont Nutrition & Bioscience). All ingredients were mixed on a Hobart 20-Quart Globe mixer for 1 minute at speed 1, then 13 minutes at speed 2. The dough temperature after mixing was between 26-27° C. The dough was then scaled into 737 g dough pieces, rested for 5 minutes at ambient temperature, and molded and sheeted on a Stickelber cross-grain molder and sheeter. After molding, the dough was transferred into four-strapped pans and proofed at 40.5° C. with 75% RH to template at a height of ½" over the pan. The dough was baked for 26 minutes at 210° C. in a Reed Oven. The final loaf temperature was verified to be 95-98°. The bread was cooled for 60 minutes at ambient temperature before putting into plastic poly bags closed with a zip tie for storage.

Example 6. Protocol for Evaluation of Softness, Resilience and Cohesiveness

Texture Profile Analysis (TPA) of Bread Firmness, resilience and cohesiveness are determined by analyzing bread slices by Texture Profile Analysis using a Texture Analyzer from Stable Micro Systems, UK. Calculation of softness, resilience, and adhesiveness are done according to preset standard supplied by Stable Micro System, UK. The probe used is aluminum 35 mm round. Bread is sliced with the width of 11.0 mm. Measurement is performed by placing two bread slices on top of each other and then compressed with a dept of 15 mm. Softness (expressed in grams) is determined during the first compression as the peak value. The figure is the force needed to compress the bread slice to a dept of 15 mm. The lower the softness value, the softer the bread.

The following settings are used: Pre-Test Speed: 4 mm/s, Test Speed: 5 mm/s, Post Test Speed: 5 mm/s, Compression Distance: 15 mm, Trigger Force: 20.0 g, Time between measurements: 5.00 sec, Count: 5, Load Cell: 5 kg, Trigger Type: Auto—20.0 g. The mode of compression is a modification to the one used in Standard method AACC 74-09. The sample is compressed twice in the test. This assay may be referred to as the "Softness Evaluation Protocol".

Protocol for Evaluation of Resilience

Area under the curve is a measure of work applied during the test. The area under the curve in the compression part (A1) and the withdrawal part (A2) during the first compression are determined from the curve generated during the first compression. The ratio between A2 and A1 is defined as the resilience of the sample and is expressed as Resilience Units (A2/A1). True elastic material will give a symmetric curve, as the force applied during the first part will be equal to the force in the second part. For bread and bread-like material, A2 is normally smaller than A1 due to disturbance of the structure during compression. Hence, resilience is always lower than 1. This assay may be referred to as the "Resilience Evaluation Protocol".

Protocol for Evaluation of Adhesiveness

The Adhesiveness is defined as the negative area of the curve after the withdrawal of the probe. Thus, the area of curved defined by negative force. The larger negative area associated with a negative compression force, the larger negative value of adhesiveness given in the units g s. For bread and bread-like material Adhesiveness is always lower than 0. This assay may be referred to as the "Adhesiveness Evaluation Protocol".

Protocol for Evaluation of Cohesiveness

The Cohesiveness is defined as the ratio between the area under second compression to the area under first compression (A3/A1+A2) and is expressed as Cohesiveness Units. It is a measure of the decay of the sample during compression. The higher the ability of the sample to regain its shape after first compression the closer the value will be to 1. For bread and bread-like material Cohesiveness is always lower than 1. This assay may be referred to as the "Cohesiveness Evaluation Protocol".

Example 7. G4 Amylase Assays

Betamyl Activity Assay

One Betamyl unit is defined as activity degrading 0.0351 mmole per 1 min. of PNP-coupled maltopentaose so that 0.0351 mmole PNP per 1 min. can be released by excess alpha-glucosidase in the assay mix. The assay mix contains 50 ul 50 mM Na-citrate, 5 mM $CaCl_2$, pH 6.5 with 25 ul enzyme sample and 25 ul Betamyl substrate (Glc5-PNP and alpha-glucosidase) from Megazyme, Ireland (1 vial dissolved in 10 ml water). The assay mix is incubated for 30 min. at 40 C and then stopped by adding 150 ul 4% Tris. Absorbance at 420 nm is measured using an ELISA-reader and the Betamyl activity is calculated based on Activity=A420*d in Betamyl units/ml of enzyme sample assayed.

Example 8. Glucoamylase Assays

Amyloglucosidase Activity Assay

One unit of amyloglucosidase activity (AGU) is defined as the amount of enzyme required to release ½ μmol of glucose per minute at a concentration of 5 mg of maltose substrate per ml of 0.05 M Na-acetate buffer, pH 5.0 at 40° C. 500 μL of the amyloglucosidase (AMG, synonymous with glucoamylase) sample is mixed with 4.7 mL 0.5% (w/v) maltose in 0.05 M Na-acetate buffer, pH 5.0. The assay mix is incubated for at least 5 min. at 40° C. and then stopped by adding 200 ul 0.1 M HCl. The α-D-glucose formed by maltose hydrolysis is following phosphorylated by ATP, in a reaction catalyzed by hexokinase and again oxidized to 6-phosphogluconate by glucose-6-phosphate dehydrogenase (VWR, Glucose Hexokinase kit). In this same reaction an equimolar amount of NAD+ is reduced to NADH and the resulting glucose increase may be quantified from an absorbance at 340 nm, using a glucose standard. Buffer without enzyme is used as blank.

Example 9. Baking Trials with Combinations of G4 Amylase and Glucoamylase

Baking trials were carried out with a standard white bread straight dough recipe 1 for US toast, according to the description in example 3. Bread was baked with G4 alpha amylase and in addition with and without a glucoamylase to evaluate anti-stailing properties of the bread by the combination of enzyme types. For this purpose, two G4 amylases: a G4 alpha amylase variant 1 PsAA_1 (GRINDAMYL CAPTIVE TS-E 1514, DuPont Nutrition Bioscience, Denmark) and a G4 alpha amylase variant 2, PsAA_2 (Powerfresh Bread 8100, DuPont Nutrition Bioscience, Denmark) were combined individually with two glucoamylases respectively: a glucoamylase from *Penicillium* sp., PspGA (5477 AGU/g) and a glucoamylase from *Rasamsonia emmersonii*, ReGA (6358 AGU/g). In addition, the glucoamylases were tested in a low and a high dosage. A dosage of 600 ppm GRINDAMYL CAPTIVE TS-E 1514 (50000 Betamyl units/g) and 147 ppm Powerfresh Bread 8100 (94050 Betamyl units/g) based on the amount flour were applied. PspGA and ReGA were individually applied at a low dosage of 7054 and 5919 AGU respectively, and high dosage of 14109 and 11839 AGU respectively per kg of flour.

The TPA result on softness and resilience of the baking trials are shown in table 1 and 2 according procedure as given in example 6 by Softness Evaluation Protocol and Resilience Evaluation Protocol. Table 1 shows the absolute measurements and table 2 the relative measurements when G4 amylase+GA is compared to the respective G4 amylase alone. It is clear from both tables, that the addition of glucoamylase together with G4 amylase as compared to G4 amylase alone clearly improves bread resilience over the testing days by increasing the measured average bread resilience units (A2/A1). These observations are valid for both low and high dose of glucoamylase with the G4 amylases as compared to G4 amylase alone. Here there do not seem to be a correlation between the amount of glucoamylase added with G4 amylase and increase in resilience obtained.

In addition, the TPA results on Cohesiveness is shown in table 3. It is here clear that the significantly improved Cohesiveness units is seen for all combinations of G4 amylase with GA as compared to the G4 amylase alone. The improvement is seen for all testing days (1, 7 and 14) and seems to increase with increased dosage of GA. The cohesiveness unit value reflects the ability of the bread to regain its shape after compression, thus the combinations of G4 amylase with GA improves of the bread foldability.

TABLE 1

TPA analysis of white toast bread made with various combinations of G4 alpha-amylase and glucoamylase evaluated at day 1, 7 and 14 by softness and resilience according to procedure given in example 6. Enzyme activity units given per kg flour.

| Trial no. | Bread | Enzymes | Softness | | | Resilience | | |
|---|---|---|---|---|---|---|---|---|
| | | | Day 1 | Day 7 force in g | Day 14 | Day 1 | Day 7 | Day 14 |
| 1 | 1 | PsAA_1 (30000 Betamyl U) | | 1492 | 1746 | | 0.166 | 0.135 |
| | 2 | PsAA_1 (30000 Betamyl U) + PspGA1 (7054 AGU) | | 1691 | 1953 | | 0.204 | 0.172 |
| | 3 | PsAA_1 (30000 Betamyl U) + PspGA1 (14109 AGU) | | 1399 | 1759 | | 0.182 | 0.154 |
| | 5 | PsAA_2 (13825 Betamyl U) | | 1272 | 1405 | | 0.225 | 0.183 |
| | 6 | PsAA_2 (13825 Betamyl U) + low PspGA1 (7054 AGU) | | 1423 | 1376 | | 0.227 | 0.234 |
| | 7 | PsAA_2 (13825 Betamyl U) + PspGA1 (14109 AGU) | | 1223 | 1447 | | 0.210 | 0.190 |
| 2 | 1 | PsAA_1 (30000 Betamyl U) | 1300 | 1839 | 2226 | 0.244 | 0.141 | 0.124 |
| | 2 | PsAA_1 (30000 Betamyl U) + ReGA (5919 AGU) | 1289 | 1854 | 1831 | 0.275 | 0.144 | 0.148 |
| | 3 | PsAA_1 (30000 Betamyl U) + ReGA (11839 AGU) | 1174 | 1955 | 2238 | 0.270 | 0.146 | 0.130 |
| | 5 | PsAA_2 (13825 Betamyl U) | 1398 | 1711 | 1789 | 0.281 | 0.170 | 0.149 |
| | 6 | PsAA_2 (13825 Betamyl U) + ReGA (5919 AGU) | 1057 | 1557 | 1607 | 0.265 | 0.173 | 0.163 |
| | 7 | PsAA_2 (13825 Betamyl U) + ReGA (11839 AGU) | 1207 | 1565 | 1526 | 0.267 | 0.192 | 0.197 |

TABLE 2

TPA analysis of white toast bread made with various combinations of G4 alpha-amylase and glucoamylase evaluated at day 1, 7 and 14 by relative softness and relative resilience (in %), as when bread made with G4 alpha-amylase and glucoamylase is compared with bread made just with G4 alpha-amylase respectively. Enzyme activity units given per kg flour.

| Trial no. | Bread | | Relative Softness | | | Relative Resilience | | |
|---|---|---|---|---|---|---|---|---|
| | | | Day 1 | Day 7 in % | Day 14 | Day 1 | Day 7 in % | Day 14 |
| 1 | 1 | PsAA_1 (30000 Betamyl U) | | 100 | 100 | | 100 | 100 |
| | 2 | PsAA_1 (30000 Betamyl U) + PspGA1 (7054 AGU) | | 113 | 112 | | 123 | 127 |
| | 3 | PsAA_1 (30000 Betamyl U) + PspGA1 (14109 AGU) | | 94 | 101 | | 109 | 114 |
| | 5 | PsAA_2 (13825 Betamyl U) | | 100 | 100 | | 100 | 100 |
| | 6 | PsAA_2 (13825 Betamyl U) + PspGA1 (7054 AGU) | | 112 | 98 | | 101 | 128 |
| | 7 | PsAA_2 (13825 Betamyl U) + PspGA1 (14109 AGU) | | 96 | 103 | | 93 | 104 |
| 2 | 1 | PsAA_1 (30000 Betamyl U) | 100 | 100 | 100 | 100 | 100 | 100 |
| | 2 | PsAA_1 (30000 Betamyl U) + ReGA (5919 AGU) | 99 | 101 | 82 | 113 | 102 | 119 |

TABLE 2-continued

TPA analysis of white toast bread made with various combinations of G4 alpha-
amylase and glucoamylase evaluated at day 1, 7 and 14 by relative softness and relative
resilience (in %), as when bread made with G4 alpha-amylase and glucoamylase is compared
with bread made just with G4 alpha-amylase respectively. Enzyme activity units given per kg
flour.

| | | Relative Softness | | | Relative Resilience | | |
|---|---|---|---|---|---|---|---|
| Trial no. | Bread | Day 1 | Day 7 in % | Day 14 | Day 1 | Day 7 in % | Day 14 |
| 3 | PsAA_1 (30000 Betamyl U) + ReGA (11839 AGU) | 90 | 106 | 101 | 111 | 103 | 105 |
| 5 | PsAA_2 (13825 Betamyl U) | 100 | 100 | 100 | 100 | 100 | 100 |
| 6 | PsAA_2 (13825 Betamyl U) + ReGA (5919 AGU) | 76 | 91 | 90 | 94 | 102 | 109 |
| 7 | PsAA_2 (13825 Betamyl U) + ReGA (11839 AGU) | 86 | 92 | 85 | 95 | 113 | 132 |

TABLE 3

TPA analysis of white toast bread made with various combinations of G4 alpha-
amylase and glucoamylase evaluated at day 1, 7 and 14 by cohesiveness according to
procedure given in example 5. The relative cohesiveness (in %), is determined by
cohesiveness of bread made with G4 alpha-amylase and glucoamylase is compared with
bread made just with G4 alpha-amylase respectively. Enzyme activity units given per kg
flour.

| | | Cohesiveness | | | Relative Cohesiveness | | |
|---|---|---|---|---|---|---|---|
| Trial no. Bread | | Day 1 | Day 7 | Day 14 | Day 1 | Day 7 | Day 14 |
| | | Cohesiveness Units | | | in % | | |
| 1 | 1 PsAA_1 (30000 Betamyl U) | | 0.368 | 0.371 | | 100 | 100 |
| | 2 PsAA_1 (30000 Betamyl U) + PspGA1 (7054 AGU) | | 0.432 | 0.383 | | 117 | 103 |
| | 3 PsAA_1 (30000 Betamyl U) + PspGA1 (14109 AGU | | 0.501 | 0.440 | | 136 | 119 |
| | 5 PsAA_2 (13825 Betamyl U) | | 0.435 | 0.430 | | 100 | 100 |
| | 6 PsAA_2 (13825 Betamyl U) + PspGA1 (7054 AGU AGU) | | 0.557 | 0.464 | | 128 | 108 |
| | 7 PsAA_2 (13825 Betamyl U) + PspGA1 (14109 AGU) | | 0.532 | 0.563 | | 122 | 131 |
| 2 | 1 PsAA_1 (30000 Betamyl U) | 0.611 | 0.397 | 0.365 | 100 | 100 | 100 |
| | 2 PsAA_1 (30000 Betamyl U) + ReGA (5919 AGU) | 0.632 | 0.402 | 0.415 | 103 | 101 | 114 |
| | 3 PsAA_1 (30000 Betamyl U) + ReGA (11839 AGU) | 0.630 | 0.398 | 0.387 | 103 | 100 | 106 |
| | 5 PsAA_2 (13825 Betamyl U) | 0.631 | 0.460 | 0.413 | 100 | 100 | 100 |
| | 6 PsAA_2 (13825 Betamyl U) + ReGA (5919 AGU) | 0.649 | 0.469 | 0.455 | 231 | 102 | 110 |
| | 7 PsAA_2 (13825 Betamyl U) + ReGA (11839 AGU) | 0.646 | 0.521 | 0.529 | 229 | 113 | 128 |

Example 10. Baking Trials with Combinations of G4 Amylases and TrGA in a Typical White Pan Bread with 8% Sugar Baking trials were carried out with a standard white bread straight dough recipe for US toast, according to the description in example 4. Bread was baked with G4 alpha amylase and in addition with and without a glucoamylase to evaluate anti-stailing properties of the bread by the combination of enzyme types. For this purpose, two G4 amylases: a G4 alpha amylase variant 1 PsAA_1 (GRINDAMYL CAPTIVE TS-E 1514, DuPont Nutrition Bioscience, Denmark) and a G4 alpha amylase variant 2, PsAA_2 (Powerfresh Bread 8100, DuPont Nutrition Bioscience, Denmark) were combined individually (same activities as given in example 9) with the glucoamylase. *Trichoderma reesei*, TrGA. TrGA was applied at a low dosage of 12272 and high dosage of 27869 AGU per kg of flour.

The results of TPA analysis of bread with 8% sugar at day 1 and 7 are shown in table 4 (absolute values) and table 5 (relative values to only G4 alpha amylase). It is clear from the results that, the added combination of glucoamylase and a G4 amylase improves resilience of the bread as seen by increased resilience units (A2/A1) compared to only adding the G4 anti-staling amylase.

TABLE 4

TPA analysis of 8% sugar white pan bread made with combinations of alpha-amylase and glucoamylase evaluated at day 1 and 7 by softness, resilience, and adhesiveness according to the procedure in example 6. Enzyme activity units given per kg flour.

| Trial no. | | 8% sugar formula Enzymes | Softness Day 1 | Day 7 | Resilience Day 1 | Day 7 | Adhesiveness Day 1 | Day 7 |
|---|---|---|---|---|---|---|---|---|
| 1 | 1 | PsAA_2 (13825 Betamyl U) | 496 | 638.93 | 0.325 | 0.216 | −1.38 | −1.13 |
| | 2 | PsAA_2 (13825 Betamyl U) with TrGA (12272 AGU) | 413.78 | 601.19 | 0.342 | 0.266 | −1.729 | −0.736 |
| 2 | 5 | PsAA_1 (30000 Betamyl U) | 641.5 | 844.6 | 0.309 | 0.141 | −0.824 | −1.01 |
| | 6 | PsAA_1 (30000 Betamyl U) with TrGA (12272 AGU) | 544.4 | 854.4 | 0.358 | 0.167 | −0.839 | −0.322 |
| | 7 | PsAA_1 (30000 Betamyl U) with TrGA (27869 AGU) | 571.8 | 832.5 | 0.352 | 0.218 | −0.391 | −0.24 |

TABLE 5

TPA analysis of 8% sugar white pan bread made with combinations of alpha-amylase and glucoamylase evaluated at day 1 and 7 by relative softness and relative resilience (in %), as when bread made with alpha-amylase and glucoamylase is compared with bread made just with alpha-amylase respectively. Enzyme activity units given per kg flour.

| Trial no. | | 8% sugar formula Enzymes | % Relative Softness Day 1 | Day 7 | % Relative Resilience Day 1 | Day 7 |
|---|---|---|---|---|---|---|
| 1 | 1 | PsAA_2 (13825 Betamyl U) | 100 | 100 | 100 | 100 |
| | 2 | PsAA_2 (13825 Betamyl U) with TrGA (12272 AGU) | 83.4 | 94 | 105.2 | 123.1 |
| 2 | 5 | PsAA_1 (30000 Betamyl U) | 100 | 100 | 100 | 100 |
| | 6 | PsAA_1 (30000 Betamyl U) with TrGA (12272 AGU) | 85 | 101 | 115.9 | 118.4 |
| | 7 | PsAA_1 (30000 Betamyl U) with TrGA (27869 AGU) | 89 | 98.5 | 114 | 155 |

33

Example 11. Baking Trials with Combinations of G4 and G+ Amylase and TrGA in a Typical Lean White Pan Bread with 1% Sugar Baking trials were carried out with a lean dough white bread straight dough recipe 3 for US toast, according to the description in example 5. Bread was baked with G4 alpha amylase and in addition with and without a glucoamylase to evaluate anti-staling properties of the bread by the combination of enzyme types. For this purpose, two G4 amylases: a G4 alpha amylase variant 1 PsAA_1 (GRINDAMYL CAPTIVE TS-E 1514, DuPont Nutrition Bioscience, Denmark) and a G4 alpha amylase variant 2, PsAA_2 (Powerfresh 8100, DuPont Nutrition Bioscience, Denmark) were combined individually with the glucoamylase from *Trichoderma reesei*, TrGA. A dosage of 600 ppm GRINDAMYL CAPTIVE TS-E 1514 (50000 Betamyl units/g) and 147 ppm Powerfresh Bread 8100 (94050 Betamyl units/g) based on the amount flour were applied. TrGA was applied at a low dosage of 12272 and high dosage of 27869 AGU per kg of flour.

The results of TPA analysis of bread with 1% sugar at day 1, 7 and 11 are shown in table 6 (absolute values) and table 7 (relative values to only G4 alpha amylase). The added combination of glucoamylase and a G4 amylase improves resilience of the bread as seen by the increased resilience units (A2/A1) compared to only adding the G4 anti-staling amylase.

TABLE 6

TPA analysis of 1% sugar white pan bread made with combinations of alpha-amylase and glucoamylase evaluated at day 1 and 7 by softness, resilience, and adhesiveness according to the procedure in example 6. Enzyme activity units given per kg flour.

| Trial no. | | 1% sugar formula Enzymes | Softness | | | Resilience | | | Adhesiveness | | |
|---|---|---|---|---|---|---|---|---|---|---|---|
| | | | Day 1 | Day 7 | Day 11 | Day 1 | Day 7 | Day 14 | Day 1 | Day 7 | Day 11 |
| 1 | 1 | PsAA_2 (13825 Betamyl U) | 247.01 | 409.8 | 1085.07 | 0.328 | 0.219 | 0.18 | −2.23 | −0.591 | −1.322 |
| | 2 | PsAA_2 (13825 Betamyl U) with TrGA (12272 AGU) | 205.8 | 255.4 | 562.23 | 0.373 | 0.303 | 0.278 | −1.451 | −0.74 | −0.793 |
| 2 | 3 | PsAA_1 (30000 Betamyl U) | 305.97 | | | 0.335 | | | −0.0707 | | |
| | 4 | PsAA_1 (30000 Betamyl U) with TrGA (12272 AGU) | 271.08 | 384.4 | 491.56 | 0.353 | 0.194 | 0.169 | −0.349 | −0.9 | −0.89 |
| | 5 | PsAA_1 (30000 Betamyl U) with TrGA (27869 AGU) | 275.11 | 416.06 | 494.9 | 0.383 | 0.247 | 0.215 | −0.39 | −0.23 | −0.43 |

TABLE 7

TPA analysis of 1% sugar white pan bread made with combinations of alpha-amylase and glucoamylase evaluated at day 1 and 7 by relative softness and relative resilience (in %), as when bread made with alpha-amylase and glucoamylase is compared with bread made just with alpha-amylase respectively. Enzyme activity units given per kg flour.

| Trial no. | | 1% sugar formula Enzymes | Softness | | | Resilience | | |
|---|---|---|---|---|---|---|---|---|
| | | | Day 1 | Day 7 | Day 11 | Day 1 | Day 7 | Day 14 |
| 1 | 1 | PsAA_2 (13825 Betamyl U) | 100 | 100 | 100 | 100 | 100 | 100 |
| | 2 | PsAA_2 (13825 Betamyl U) with TrGA (12272 AGU) | 83.3 | 62.3 | 51.8 | 113.7 | 138.4 | 154.4 |
| 2 | 3 | PsAA_1 (30000 Betamyl U) | 100 | NA | NA | 100 | NA | NA |
| | 4 | PsAA_1 (30000 Betamyl U) with TrGA (12272 AGU) | 88.6 | NA | NA | 105.4 | NA | NA |

TABLE 7-continued

TPA analysis of 1% sugar white pan bread made with combinations of alpha-amylase and glucoamylase evaluated at day 1 and 7 by relative softness and relative resilience (in %), as when bread made with alpha-amylase and glucoamylase is compared with bread made just with alpha-amylase respectively. Enzyme activity units given per kg flour.

| 1% sugar formula | | Softness | | | Resilience | | |
|---|---|---|---|---|---|---|---|
| Trial no. | Enzymes | Day 1 | Day 7 | Day 11 | Day 1 | Day 7 | Day 14 |
| 5 | PsAA_1 (30000 Betamyl U) with TrGA (27869 AGU) | 89.9 | NA | NA | 114.3 | NA | NA |

Example 12. Protocol for Evaluating Crust Color Using Lab Values

The color of the loaf of bread is evaluated by using a handheld colorimeter called the BC-10 plus Baking meter from Konica Minoita. L*a*b* values are measured. After the bread has been baked and cooled for one hour at ambient temperature, the loaf of bread was evaluated. First, a white calibration is performed using the provided white calibration cap. This calibration is done in the same temperature conditions as the samples. When the colorimeter has adapted to the ambient temperature, it is ready for measurement. The aperture is set on the sample and the reading is recorded. An average of 4 readings per loaf were done. The results are given for a Lab color spectrum. L* for the lightness from black (0) to white (100), a* form green (–) to red (+), and b* from blue (–) to yellow (+). Bread was prepared as in example 10 and the Crust color measured, see results in table 8. It can be seen that the color of the loaf is getting darker and browner by the addition of G4 amylase and glucoamylase as compared to only adding G4 amylase.

TABLE 8

The Crust color was taken using the BC-10 plus Baking meter from Konica Minolta according to Example 10. Enzyme activity units given per kg flour.

| | L*a*b* values 8% sugar Formula | | | L*a*b* values 1% sugar Formula | | |
|---|---|---|---|---|---|---|
| Enzyme | L* | a* | b* | L* | a* | b* |
| PsAA_1 (30000 Betamyl U) | 50.1 | 13.8 | 16.9 | 58.5 | 15.7 | 34.5 |
| PsAA_1 (30000 Betamyl U) + TrGA (12272 AGU) | 37.8 | 17.7 | 24.6 | 49.3 | 17.3 | 32.1 |
| PsAA_1 (30000 Betamyl U) + TrGA (27869 AGU) | 36.9 | 17.8 | 24.5 | 50.1 | 18.4 | 34.4 |

Example 13. Protocol for Evaluating Bread Heights

Bread height was measured after baking and cooling for one hour at ambient temperature. Heights were taken by placing a caliper in the center of the loaf and reading the measurement. Heights were done on an average of four loaves.

The results bread height measurements of bread with 1% and 8% sugar are shown in table 9 (absolute values) and table 10 (relative values to only G4 alpha amylase). It can be seen, that adding G4 amylase and glucoamylase increase the bread height as compared to only adding G4 amylase.

TABLE 9

Heights of the bread (inches) with combinations of alpha-amylase and glucoamylase evaluated one hour after baking. Enzyme activity units given per kg flour.

| Trial no. | | | Height of bread with 8% sugar (inches) | Height of bread with 1% sugar (inches) |
|---|---|---|---|---|
| 1 | 1 | PsAA_2 (13825 Betamyl U) | 4.76 | 4.66 |
| | 2 | PsAA_2 (13825 Betamyl U) with TrGA (12272 AGU) | 4.79 | 5.25 |
| 2 | 3 | PsAA_1 (30000 Betamyl U) | 4.8 | 4.94 |
| | 4 | PsAA_1 (30000 Betamyl U) with TrGA (12272 AGU) | 4.79 | 5.09 |
| | 5 | PsAA_1 (30000 Betamyl U) with TrGA (27869 AGU) | 4.88 | 5.1 |

TABLE 10

Relative heights of the bread with combinations of alpha-amylase and glucoamylase evaluated one hour after baking (in %), as when bread made with alpha-amylase and glucoamylase is compared with bread made just with alpha-amylase respectively. Enzyme activity units given per kg flour.

| Trial no. | | | Relative % Height in bread with 8% sugar | Relative % Height in bread with 1% sugar |
|---|---|---|---|---|
| 1 | 1 | PsAA_2 (13825 Betamyl U) | 100 | 100 |
| | 2 | PsAA_2 (13825 Betamyl U) with TrGA (12272 AGU) | 100.6 | 112.7 |
| 2 | 3 | PsAA_1 (30000 Betamyl U) | 100 | 100 |
| | 4 | PsAA_1 (30000 Betamyl U) with TrGA (12272 AGU) | 99.8 | 103 |
| | 5 | PsAA_1 (30000 Betamyl U) with TrGA (27869 AGU) | 102 | 103.2 |

What is claimed is:

1. A process for making a baked product with improved resilience, comprising adding to a dough comprising flour, water and a leavening agent, a nonmaltogenic exoamylase, wherein said nonmaltogenic exoamylase is an enzyme having at least 70%, 80%, 85%, 90%, 95%, 98%, 99% or 100% sequence identity to SEQ ID NO:1 or SEQ ID NO:2 and is present in an amount from about 15,000 to about 40,000 Betamyl Units per Kg of flour, and a glucoamylase, wherein said glucoamylase is an enzyme having at least 70%, 80%, 85%, 90%, 95%, 98%, 99% or 100% sequence identity to SEQ ID NO:3 and is present in an amount from about 5,000 to about 10,000 amyloglucosidase activity units (AGU) per Kg of flour, and baking the dough, wherein improved resilience means an increase in resilience measured as TPA resilience (A2/A1) relative to a corresponding baked product without the added nonmaltogenic exoamylase and glucoamylase under otherwise identical conditions.

2. The process of claim 1 further comprising adding a third enzyme selected from the group of consisting of oxidoreductases, hydrolases, lipases, esterases, glycosidases, amylases, maltogenic alpha-amylases, pullulanases, xylanases, cellulases, hemicellulases, starch degrading enzymes, proteases and lipoxygenases.

3. A dough comprising flour, a non-maltogenic exoamylase, wherein the nonmaltogenic exoamylase is an enzyme having at least 70%, 80%, 85%, 90%, 95%, 98%, 99% or 100% sequence identity to SEQ ID NO:1 or SEQ ID NO:2 and is present in an amount from about 15,000 to about 40,000 Betamyl Units per Kg of flour, and a glucoamylase, wherein the glucoamylase is an enzyme having at least 70%, 80%, 85%, 90%, 95%, 98%, 99% or 100% sequence identity to SEQ ID NO:3 and is present in an amount from about 5,000 to about 10,000 amyloglucosidase activity units (AGU) per Kg of flour.

4. The dough of claim 3 further comprising a third enzyme selected from the group of consisting of oxidoreductases, hydrolases, lipases, esterases, glycosidases, amylases, maltogenic alpha-amylases, pullulanases, xylanases, cellulases, hemicellulases, starch degrading enzymes, proteases and lipoxygenases.

5. The dough of claim 4 wherein the third enzyme is a maltogenic alpha-amylase.

6. The dough of claim 5 which has been baked.

* * * * *